US009532841B2

United States Patent
Stern et al.

(10) Patent No.: US 9,532,841 B2
(45) Date of Patent: *Jan. 3, 2017

(54) AUTOFOCUS AND/OR AUTOSCALING IN TELESURGERY

(71) Applicant: Intuitive Surgical Operations, Inc., Sunnyvale, CA (US)

(72) Inventors: John D. Stern, Menlo Park, CA (US); Robert G. Younge, Portola Valley, CA (US); David S. Gere, Palo Alto, CA (US); Gunter D. Niemeyer, Pasadena, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 77 days.

This patent is subject to a terminal disclaimer.

(21) Appl. No.: 14/225,805

(22) Filed: Mar. 26, 2014

(65) Prior Publication Data

US 2014/0296870 A1 Oct. 2, 2014

Related U.S. Application Data

(63) Continuation of application No. 13/324,746, filed on Dec. 13, 2011, now Pat. No. 8,715,167, which is a (Continued)

(51) Int. Cl.
*A61B 1/00* (2006.01)
*A61B 19/00* (2006.01)
*A61B 17/00* (2006.01)

(52) U.S. Cl.
CPC ....... *A61B 19/2203* (2013.01); *A61B 1/00188* (2013.01); *A61B 34/30* (2016.02);
(Continued)

(58) Field of Classification Search
CPC . A61B 19/2203; A61B 19/22; A61B 19/5212; A61B 2019/223; A61B 2019/2223; A61B 2019/2234; A61B 2019/2296; A61B 2017/00477; A61B 1/00188
See application file for complete search history.

(56) References Cited

U.S. PATENT DOCUMENTS 4,277,130 A * 7/1981 Takahashi ............ G02B 21/361
359/363
5,140,458 A 8/1992 Takagi et al.
(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Bo J Peng

(57) ABSTRACT

Robotic, telerobotic, and/or telesurgical devices, systems, and methods take advantage of robotic structures and data to calculate changes in the focus of an image capture device in response to movement of the image capture device, a robotic end effector, or the like. As the size of an image of an object shown in the display device varies with changes in a separation distance between that object and the image capture device used to capture the image, a scale factor between a movement command input may be changed in response to moving an input device or a corresponding master/slave robotic movement command of the system. This may enhance the perceived correlation between the input commands and the robotic movements as they appear in the image presented to the system operator.

17 Claims, 15 Drawing Sheets

Related U.S. Application Data continuation of application No. 11/239,661, filed on Sep. 29, 2005, now Pat. No. 8,079,950.

(52) U.S. Cl.
CPC .............. *A61B 34/35* (2016.02); *A61B 34/37* (2016.02); *A61B 34/70* (2016.02); *A61B 34/77* (2016.02); *A61B 90/361* (2016.02); *A61B 2017/00477* (2013.01); *A61B 2034/305* (2016.02)

(56) References Cited

U.S. PATENT DOCUMENTS

| | | | |
|---|---|---|---|
| 5,217,003 A | 6/1993 | Wilk | |
| 5,382,885 A | 1/1995 | Salcudean et al. | |
| 5,573,492 A | 11/1996 | Dianna et al. | |
| 5,598,269 A | 1/1997 | Kitaevich et al. | |
| 5,609,560 A | 3/1997 | Ichikawa et al. | |
| 5,662,584 A | 9/1997 | Hori et al. | |
| 5,787,886 A | 8/1998 | Kelly et al. | |
| 5,808,665 A | 9/1998 | Green | |
| 5,855,553 A | 1/1999 | Tajima et al. | |
| 5,855,583 A | 1/1999 | Wang et al. | |
| 6,224,542 B1 | 5/2001 | Chang et al. | |
| 6,327,099 B1 * | 12/2001 | Itoh | G02B 15/177 359/683 |
| 6,368,332 B1 | 4/2002 | Salcudean et al. | |
| 6,424,885 B1 | 7/2002 | Niemeyer et al. | |
| 6,434,416 B1 | 8/2002 | Mizoguchi et al. | |
| 6,587,750 B2 | 7/2003 | Gerbi et al. | |
| 6,646,541 B1 | 11/2003 | Wang et al. | |
| 6,661,571 B1 | 12/2003 | Shioda et al. | |
| 6,786,896 B1 | 9/2004 | Madhani et al. | |
| 6,793,653 B2 | 9/2004 | Sanchez et al. | |
| 6,858,003 B2 | 2/2005 | Evans et al. | |
| 6,999,852 B2 | 2/2006 | Green | |
| 7,076,286 B2 | 7/2006 | Mizoguchi et al. | |
| 7,155,316 B2 | 12/2006 | Sutherland et al. | |
| 7,492,116 B2 | 2/2009 | Oleynikov et al. | |
| 8,079,950 B2 | 12/2011 | Stern et al. | |
| 8,715,167 B2 | 5/2014 | Stern et al. | |
| 2002/0050518 A1 * | 5/2002 | Roustaei | G06K 7/10544 235/454 |
| 2002/0103500 A1 | 8/2002 | Gildenberg | |
| 2003/0114962 A1 | 6/2003 | Niemeyer | |
| 2003/0125716 A1 | 7/2003 | Wang et al. | |
| 2004/0070822 A1 | 4/2004 | Shioda et al. | |
| 2005/0083570 A1 | 4/2005 | Ueda et al. | |
| 2005/0090730 A1 | 4/2005 | Cortinovis et al. | |
| 2005/0187473 A1 | 8/2005 | Boctor et al. | |
| 2006/0100642 A1 | 5/2006 | Yang et al. | |
| 2012/0109377 A1 | 5/2012 | Stern et al. | |

* cited by examiner

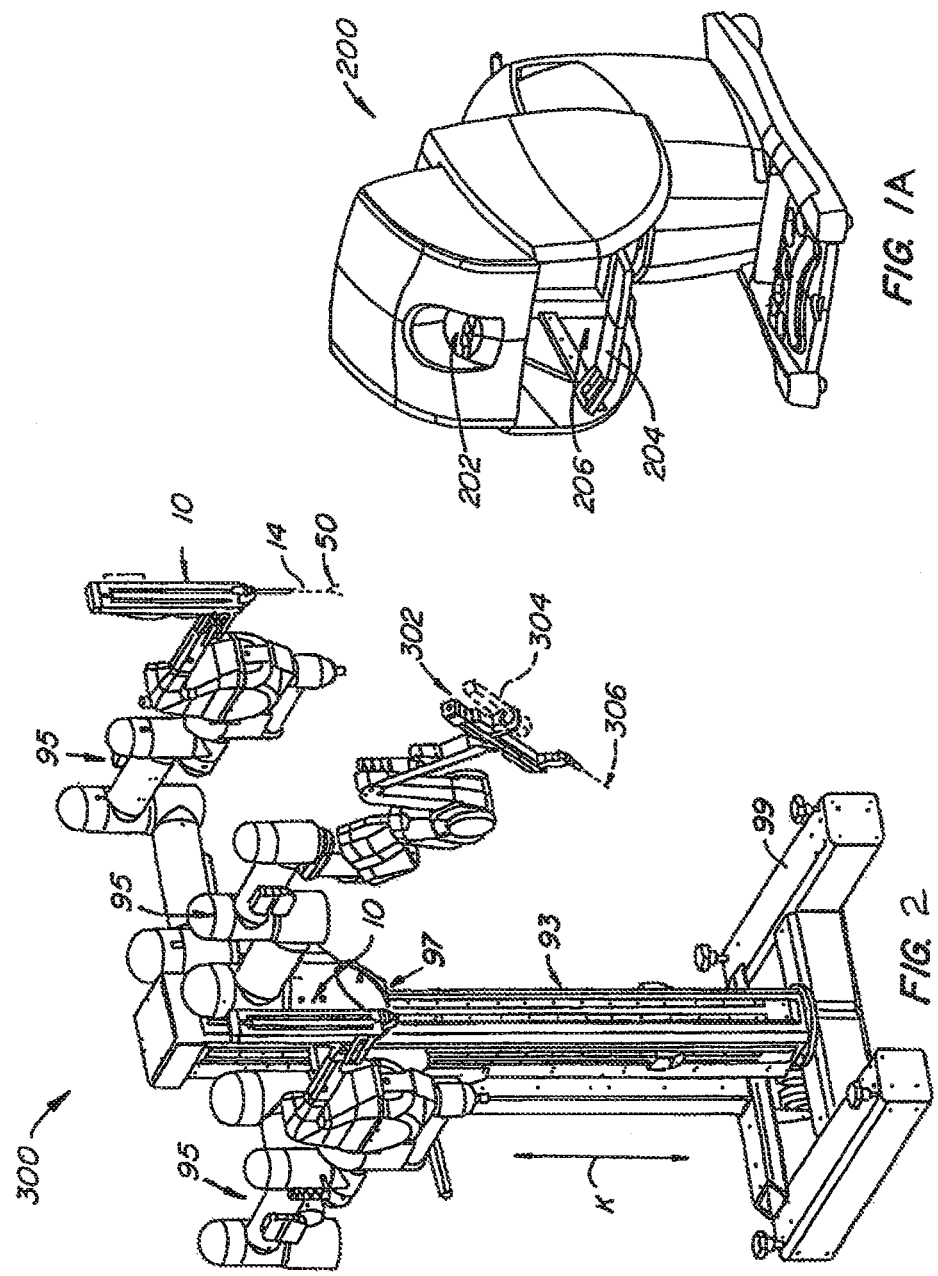

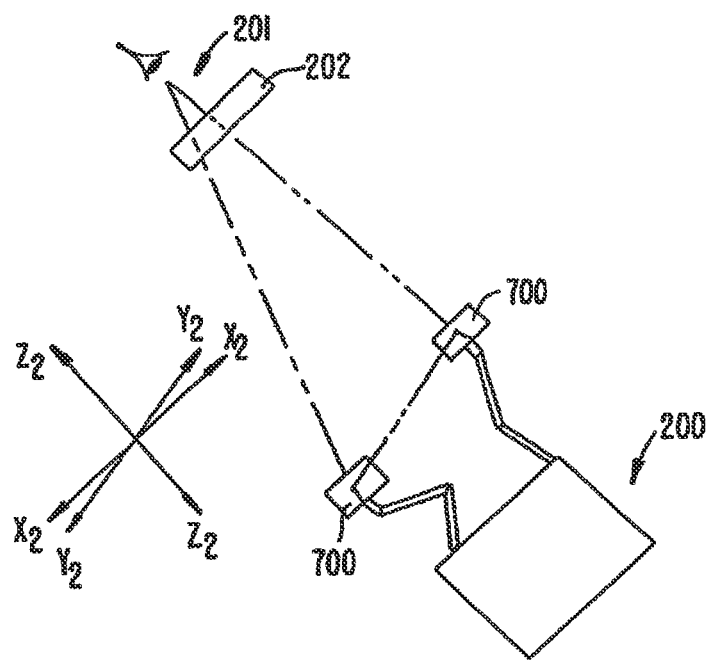
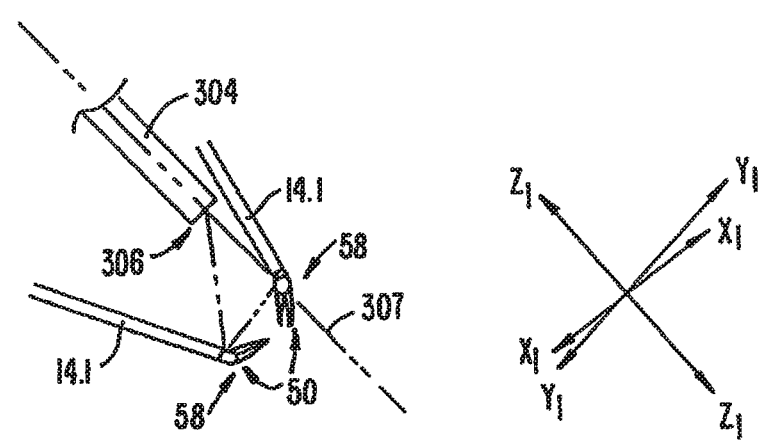
FIG. 7.

AUTOFOCUS AND/OR AUTOSCALING IN TELESURGERY

BACKGROUND OF THE INVENTION

The present invention is generally related to telesurgical devices, systems, and methods. In an exemplary embodiment, the invention provides systems and methods for robotically altering a focus, optical scaling, and/or scaling factor of a robotic surgical system in response to robotic movements, preferably so as to maintain focus at a fixed location in space during movement of an image capture device, so as to maintain focus on a moving robotic tool, or the like; and/or so as to adjust the scale of robotic end effector movements corresponding to input commands in a master/slave telerobotic system so as to compensate for the changes in scale of an object shown in a display, and the like.

Minimally invasive medical techniques are intended to reduce the amount of extraneous tissue which is damaged during diagnostic or surgical procedures, thereby reducing patient recovery time, discomfort, and deleterious side effects. One effect of minimally invasive surgery, for example, may be reduced post-operative hospital recovery times. Because the average hospital stay for a standard surgery is typically significantly longer than the average stay for an analogous minimally invasive surgery, increased use of minimally invasive techniques could save millions of dollars in hospital costs each year. While many of the surgeries performed each year in the United States could potentially be performed in a minimally invasive manner, only a portion of the current surgeries use these advantageous techniques due to limitations in minimally invasive surgical instruments and the additional surgical training involved in mastering them.

Minimally invasive robotic surgical or telesurgical systems have been developed to increase a surgeon's dexterity and avoid some of the limitations on traditional minimally invasive techniques. In telesurgery, the surgeon uses some form of remote control, e.g., a servomechanism or the like, to manipulate surgical instrument movements. In telesurgery systems, the surgeon can be provided with an image of the surgical site at the surgical workstation. While viewing a two or three dimensional image of the surgical site on a display, the surgeon performs the surgical procedures on the patient by manipulating master control devices, which in turn control motion of the servomechanically operated instruments.

The servomechanism used for telesurgery will often accept input from two master controllers (one for each of the surgeon's hands) and may include two or more robotic arms or manipulators, on each of which a surgical instrument is mounted. Operative communication between master controllers and associated robotic arm and instrument assemblies is typically achieved through a control system. The control system typically includes at least one processor which relays input commands from the master controllers to the associated robotic arm and instrument assemblies, and back from the instrument and arm assemblies to the associated master controllers (in the case of, e.g., force feedback or the like). One example of a robotic surgical system is the DaVinci® system available from Intuitive Surgical, Inc. of Mountain View, Calif.

The new telesurgical devices have significantly advanced the art, providing huge potential improvements in endoscopic procedures. However, as with many such advances, still further improvements would be desirable. In particular, it is generally beneficial to provide clear and precise displays of the surgical environment and treatments to a surgeon working with a telesurgical system. Three dimensional image displays significantly enhance the surgeon's ability to interact with the tissues and visually guide the procedure, as the visual input may be more complete (as compared to open surgical procedures) than the tactile feedback provided by some robotic systems. When placing a heightened reliance on visual input, any loss of focus by the imaging system may be particularly distracting. Additionally, while the known robotic surgical systems may provide good correlation between movement of the input devices and movement of the robotic instruments in many circumstances, the correlation might still benefit from further improvements.

In general, it would be desirable to provide improved telesurgical and/or telerobotic devices, systems, and methods. It would be, for example, advantageous to provide new approaches for maintaining clarity of the visual display presented to surgeons and other system operators of such telesurgical and telerobotic devices. It would also, for example, be helpful to provide enhanced correlations between the input movements and the robotic end effector movements calculated by the processor of the system, particularly as the configuration of the robotic procedure undergoes changes as the procedure progresses.

BRIEF SUMMARY OF THE INVENTION

The present invention generally provides improved robotic, telerobotic, and/or telesurgical devices, systems, and methods. Exemplary embodiments take advantage of the robotic structures and data of these systems, along with new and/or modified structural components, to calculate changes in the focus of an image capture device in response to movement of the image capture device, a robotic end effector, or the like. As the size of an image of an object shown in the display device varies (for example, with changes in a separation distance between that object and the image capture device used to capture the image), some embodiments may change the motion scale factor between a movement command input by moving an input device and a corresponding master/slave robotic movement command of the system. This may enhance the perceived correlation between the input commands and the robotic movements as they appear in the image presented to the system operator.

In a first aspect, the invention provides a surgical robotic system comprising a image capture device having a variable focus. A robotic linkage movably extends from the base to the image capture device, and an actuator is coupled to the variable focus of the image capture device. A processor couples the robotic linkage to the actuator. The processor transmits a command signal to the actuator in response to a movement of the linkage such that a change in the variable focus compensates for movement of the image capture device.

In another aspect, the invention provides a surgical system comprising an image capture device for capturing an image of an object. A display is coupled to the image capture device so as to show the image. A display scale of the object in the image varies with a separation distance between the object and the image capture device. A robotic linkage effects relative movement between the object and the image capture device. An input device is provided to allow a master/slave input command to be entered into the system. A processor couples the robotic linkage to the input device. The processor determines the relative movement corresponding to the movement command per a motion scale factor. The processor alters the motion scale factor in response to the relative movement so as to compensate for changes in the display scale.

In yet another aspect, the invention provides a surgical robotic method. The method comprises capturing an image of an object at a surgical site with an image capture device. The object or the image capture device is moved robotically with a relative movement. A new robotic motion scale factor or focus is determined in response to the relative movement.

BRIEF DESCRIPTION OF THE DRAWINGS

FIG. 1A shows a three dimensional view of an operator station of the telesurgical system of FIG. 1.

FIG. 2 shows a three-dimensional view of a patient-side cart or surgical station of the telesurgical system, the cart carrying three robotically controlled arms, the movement of the arms being remotely controllable from the operator station shown in FIG. 1A.

FIG. 7 shows a schematic three-dimensional drawing indicating the positions of the end effectors relative to a viewing end of an endoscope and the corresponding positions of master control devices relative to the eyes of an operator, typically a surgeon.

DETAILED DESCRIPTION OF THE INVENTION

The present invention generally provides improved robotic, telerobotic, and/or telesurgical devices, systems, and methods. Embodiments of the invention may be particularly well suited for minimally invasive or open robotic surgical procedures, often using a master/slave telesurgical system. Although this invention will often be described below in the context of a robotic, computer-enhanced surgical system, the invention may also have applications beyond robotic surgical systems to any surgical environment that utilizes a camera to provide an image of the surgical site to the surgeon, as is often provided for minimally invasive surgical procedures performed using laparoscopic instruments and the like.

Embodiments of the invention will often comprise a surgical system having a camera or other image capture device to provide an image of the surgical site for viewing by the surgeon. By including an encoder or other sensor coupled to the focusing mechanism of the camera, information can be provided that is useful in many different ways. Hence, many embodiments of the invention will include a sensor for measuring a state of the focus mechanism, the sensor typically comprising an encoder, a potentiometer, or the like coupled to the focus mechanism of the image capture device, such as to the camera head of an endoscopic camera system. For ease of reference, the following description will often refer simply to an encoder as sensing the position or state of the focusing mechanism, although a wide variety of alternative state sensing systems might also be employed. Similarly, the system will often be described with reference to an image capture device comprising an endoscope, as well as to a camera head of the image capture device, which is typically operatively connected to optical components of the image capture device. These insertable image capture devices will often include at least a portion which is suitable for positioning within a patient so as to be able to provide an image of an internal surgical site to a system operator. Advantageously, the devices, systems, and methods described herein may optionally employ significant portions of commercially available robotic surgical systems, including the DaVinci® surgical system available from Intuitive Surgical, Inc. of Sunnyvale, Calif.

Figure 1:
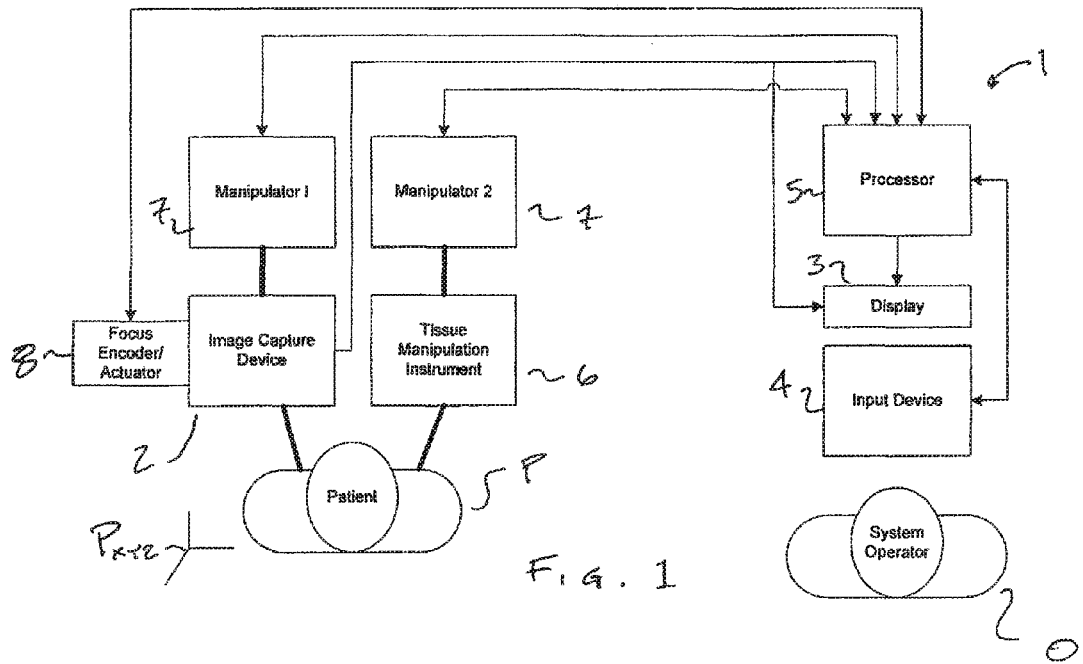
FIG. 1 is a schematic block diagram illustrating a telesurgical system in which focus and/or a motion scale factor is adjusted in response to robotic movements.

Referring now to FIG. 1, a telesurgical system 1 allows a system operator O to perform a surgical treatment on an internal tissue of patient P. An image capture device 2 preferably obtains three dimensional images of the internal tissue, and an image of the tissue is displayed to the system operator O on a display device 3. While observing the image in the display device, and by reference to that image, the system operator manipulates one or more handles of an input device 4.

In response to signals from the input device, the processor 5 calculates movement of a treatment probe or instrument 6 for manipulation of tissues. More specifically, processor 5 transmits signals corresponding to the calculated movements desired by probe 6 to an associated robotic manipulator 7, and the manipulator in response effects movement of the probe. Probe 6 will often be mounted to an instrument holder of manipulator 7, and may also include additional degrees of freedom.

Along with providing movement of treatment probe 6, telesurgical system 1 also allows movement and adjustment to image capture device 2, here using another manipulator 7. The manipulator 7 supporting the image capture device may be repositioned by system operator O through appropriate inputs into the input device 4. Processor 5 calculates appropriate movements of the manipulator 7 supporting image capture device 2 in response to these inputs, and the manipulator provides those movements in response to signals from the processor. Image capture device 2 transmits image signals to display 3, and may also provide image and/or other signals for use by processor 1, such as providing image signals for image processing techniques or the like.

As illustrated in FIG. 1, positional information from the focus encoder or other sensor of an encoder/actuator 8 is provided to processor 1 to allow the processor to determine where the camera should focus so as to allow the surgeon to continue to operate without interruption. The processor transmits focus control signals to encoder/actuator 8 using the information provided regarding the current focus state from the encoder/actuator, and also using information from manipulators 7 regarding the position or state of the image capture device 2, probe 6, and the like. In some embodiments, processor 5 may transmit signals to a focus encoder/actuator 8 so as to maintain the focus of image capture device 2 at a given location in a coordinate frame of reference of the internal surgical site of patient P, such as a point in Cartesian coordinate reference frame Pxyz. In other embodiments, the signals transmitted from processor 5 to focus encoder/actuator 8 may maintain the focus of image capture device 2 on a structure or surface of tissue manipulation instrument or probe 6. While the data path between focus encoder/actuator 8 and processor 1 is schematically shown as a separate pathway, communication between the focusing mechanism and the processor will often be handled as a multiplexed or separated channel portion of the communication between the associated manipulator 7 and the processor.

Robotic autofocus may be implemented in a variety of differing methods and systems. In many embodiments, the camera/endoscope combination will initially be adjusted to focus at a particular point in the surgical field, such as a point in reference frame Pxyz. This initial focus point can be achieved in a number of different ways. For example, while holding the camera/endoscope substantially stationary with respect to the surgical site, the surgeon may manually input focus commands so that the camera focuses on a desired location. The desired location may comprise the tip of a robotic tool, instrument, or probe at the surgical site, a portion of the surgical site itself, a coronary vessel during an anastomotic procedure, or a heart valve during a valve repair or replacement procedure (for example). Such manual focus can be achieved through the use of a surgeon input device, such as a foot pedal/switch, a manual toggle, or a voice control system that commands the camera head focusing mechanism to move until the desired point of focus is achieved.

Alternatively, the camera may automatically focus on an object within the surgical field utilizing any of a wide variety of commercially available autofocus technologies. Suitable systems may include active systems using ultrasound or infrared signals, passive image-analysis systems, and/or the like, including those described in, for example, U.S. Pat. Nos. 4,983,033, 4,602,861, and/or 4,843,416, or that included in the SX-70 rangefinder commercialized by Polaroid. The point of the initial autofocus may coincide with a sharp edge of a substantially stationary surgical instrument, or of a target located on one or more of the surgical instruments, a target attached to one or more structures of the internal surgical site, or the like. Such autofocus methods may again be achieved through an appropriate surgeon's input device, such as an initial focus button that would cause the camera/endoscope to automatically focus on the tool tips, or the like. Alternatively, the system processor could include a detector to detect when an instrument having an appropriate target was placed within the surgical field. Once the detector determines that a suitable target was present within the field, the endoscope/camera could automatically focus without having to be commanded to do so by the surgeon.

Regardless of the manner of achieving the point of initial focus (whether manual, automatic, or otherwise), this point may be referred to as the initial focus point. Upon capturing this initial focus point, the position or state occupied by the camera's focusing mechanism corresponds to this initial focus point can be known by processor 5 via the state information provided by encoder/actuator 8. System 1 can maintain that particular focus point regardless of subsequent movement by the surgeon of the image capture device 2 using a "Stay in Focus" function of processor 5. For example, the surgeon may move the image capture device 2 away from the surgical site to capture a wider field of view. Alternatively, the surgeon may move the endoscope toward the surgical site along the axis of the endoscope for a closer view. Regardless of the type of movement, the state of the focusing mechanism at the initial focus point, the particular optical parameters of the endoscope, and/or the relationship between the focus mechanism state and the focus point distance separating the endoscope from the focus point and the specific movements of the endoscope by manipulator 7 are all known. From this information, focus encoder/actuator 8 may be driven by processor 5 in response to movement of manipulator 1 so as to maintain the point of focus of image capture device 2 at a fixed point in reference frame Pxyz within patient P, with the fixed point being set as the initial focus point.

Calculation of the separation distance between a robotically moving image capture device and a particular point in space within patient P may be facilitated by tracking the motion of the manipulator 7 supporting the image capture device. Similarly, when the focus target is a surface or structure of probe 6, monitoring motion of the manipulators supporting both the image capture device and probe will allow calculation of changes in relative positioning between the image capture device and the point of focus. For example, as described in U.S. Pat. No. 6,424,885, the full disclosure of which is incorporated herein by reference, telesurgical control may be referenced into a Cartesian coordinate system, which may be coupled to the image capture device so as to maintain coordination between master/slave input commands by the system operator and the movement of tissue manipulation instruments or probe 6. The information regarding the robotic arm movements are generally known via various encoders or potentiometers of the robotic linkage, and this information is often available to the processor controlling manipulator movements, including to the DaVinci™ surgical system manufactured by Intuitive Surgical, Inc. The position information from the manipulators 7 is fed to processor 5, which can then instruct the focus encoder/actuator 8 of the focus mechanism in image capture device 2. The instruction signals from processor 5 to the focus encoder/actuator may comprise, for example, a specific number of focus encoder counts to move in a desired direction to maintain the focus at an initial focus point, a desired change in focus potentiometer reading, or the like. Exemplary structures of the processor 5, input device 4, manipulators 7, and the like for performing these techniques will be described with more detail with reference to the exemplary embodiments of FIGS. 1A-14.

Referring to FIG. 1A of the drawings, an operator station or surgeon's console of a minimally invasive telesurgical system is generally indicated by reference numeral 200. The station 200 includes a viewer 202 where an image of a surgical site is displayed in use. A support 204 is provided on which an operator, typically a surgeon, can rest his or her forearms while gripping two master controls (not shown in FIG. 1A), one in each hand. The master controls are positioned in a space 206 inwardly beyond the support 204. When using the control station 200, the surgeon typically sits in a chair in front of the control station 200, positions his or her eyes in front of the viewer 202 and grips the master controls one in each hand while resting his or her forearms on the support 204.

In FIG. 2 of the drawings, a cart or surgical station of the telesurgical system is generally indicated by reference numeral 300. In use, the cart 300 is positioned close to a patient requiring surgery and is then normally caused to remain stationary until a surgical procedure to be performed has been completed. The cart 300 typically has wheels or castors to render it mobile. The station 200 is typically positioned remote from the cart 300 and can be separated from the cart 300 by a great distance, even miles away, but will typically be used within an operating room with the cart 300.

The cart 300 typically carries three robotic arm assemblies. One of the robotic arm assemblies, indicated by reference numeral 302, is arranged to hold an image capturing device 304, e.g., a remote image device, an endoscope, or the like. Each of the two other arm assemblies 10, 10 respectively, includes a surgical instrument 14. While described in portions of the following description with reference to endoscopic instruments and/or image capture devices, many embodiments will instead include intravascular and/or orthopedic instruments and remote imaging systems.

The endoscope 304 has a viewing end 306 at a remote end of an elongate shaft thereof. It will be appreciated that the endoscope 304 has an elongate shaft to permit its viewing end 306 to be inserted through an entry port into an internal surgical site of a patient's body. The endoscope 304 is operatively connected to the viewer 202 to display an image captured at its viewing end 306 on the viewer 202. Each robotic arm assembly 10, 10 is normally operatively connected to one of the master controls. Thus, the movement of the robotic arm assemblies 10, 10 is controlled by manipulation of the master controls. The instruments 14 of the robotic arm assemblies 10, 10 have end effectors which are mounted on wrist members which are pivotally mounted on distal ends of elongate shafts of the instruments 14, as is described in greater detail hereinbelow. It will be appreciated that the instrument 14 have elongate shafts to permit the end effectors to be inserted through entry ports into the internal surgical site of a patient's body. Movement of the end effectors relative to the ends of the shafts of the instruments 14 is also, controlled by the master controls.

The robotic arms 10, 10, 302 are mounted on a carriage 97 by means of setup joint arms 95. The carriage 97 can be adjusted selectively to vary its height relative to a base 99 of the cart 300, as indicated by arrows K. The setup joint arms 95 are arranged to enable the lateral positions and orientations of the arms 10, 10, 302 to be varied relative to a vertically extending column 93 of the cart 300. Accordingly, the positions, orientations and heights of the arms 10, 10, 302 can be adjusted to facilitate passing the elongate shafts of the instruments 14 and the endoscope 304 through the entry ports to desired positions relative to the surgical site. When the surgical instruments 14 and endoscope 304 are so positioned, the setup joint arms 95 and carriage 97 are typically locked in position.

Figure 3:
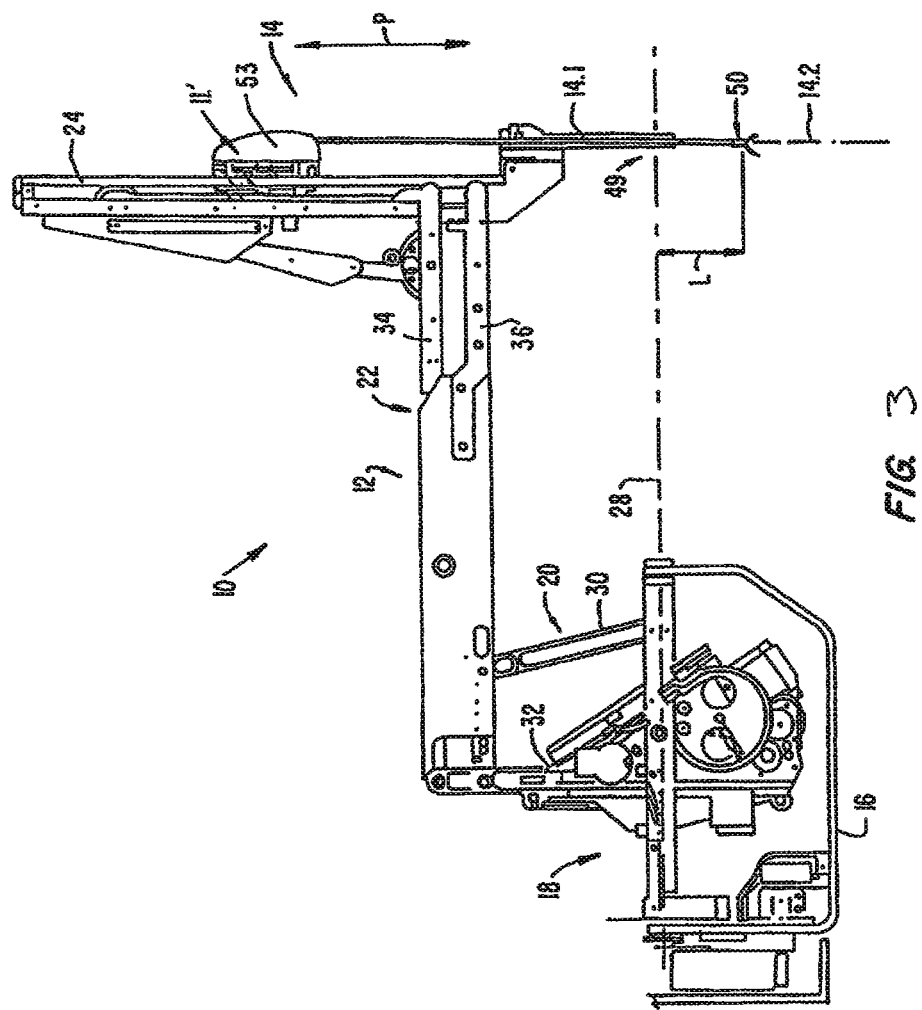
FIG. 3 shows a side view of a robotic arm and surgical instrument assembly.

In FIG. 3 of the drawings, one of the robotic arm assemblies 10 is shown in greater detail. Each assembly 10 includes an articulated robotic arm 12, and a surgical instrument, schematically and generally indicated by reference numeral 14, mounted thereon.

Figure 4:
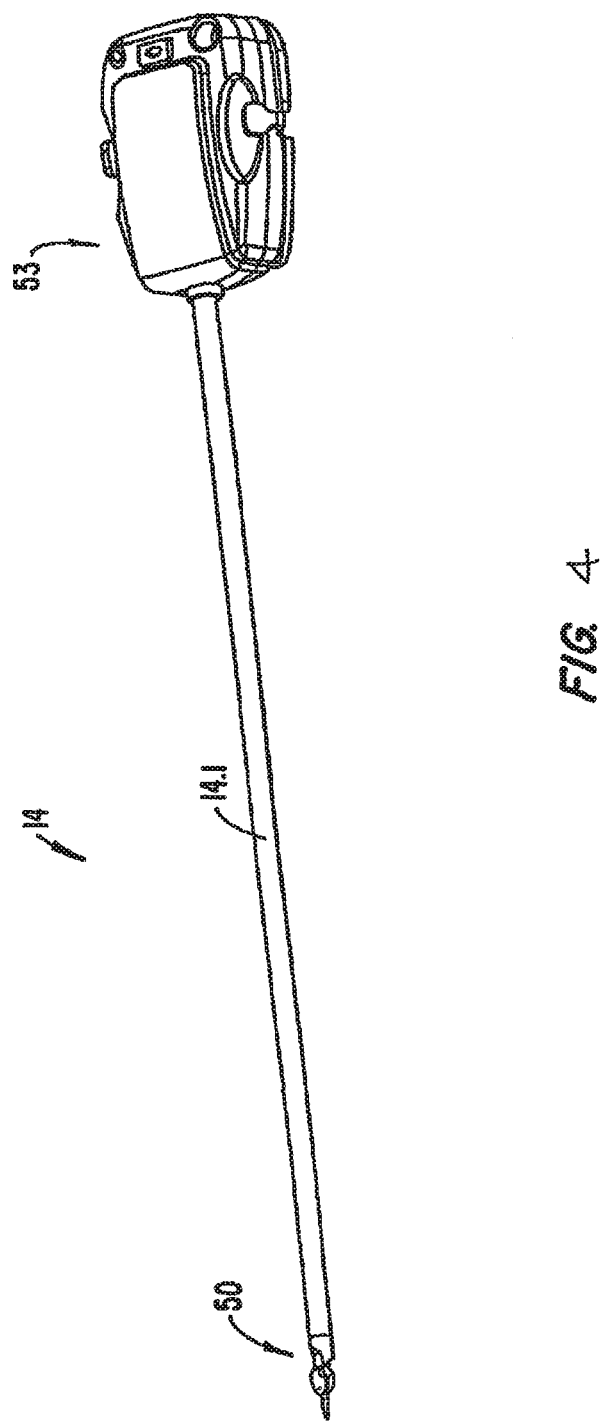
FIG. 4 shows a three-dimensional view of a surgical instrument.

FIG. 4 indicates the general appearance of the surgical instrument 14 in greater detail. The surgical instrument 14 includes an elongate shaft 14.1. The wrist-like mechanism, generally indicated by reference numeral 50, is located at a working end of the shaft 14.1. A housing 53, arranged releasably to couple the instrument to the robotic arm 12, is located at an opposed end of the shaft 14.1. In FIG. 3, and when the instrument 14 is coupled or mounted on the robotic arm 12, the shaft 14.1 extends along an axis indicated at 14.2. The instrument 14 is typically releasably mounted on a carriage 11, which can be driven to translate along a linear guide formation 24 of the arm 12 in the direction of arrows P.

The robotic arm 12 is typically mounted on a base or platform at an end of its associated setup joint arm 95 by means of a bracket or mounting plate 16. The robotic arm 12 includes a cradle, generally indicated at 18, an upper arm portion 20, a forearm portion 22 and the guide formation 24. The cradle 18 is pivotally mounted on the plate 16 in a gimbaled fashion to permit rocking movement of the cradle 18 about a pivot axis 28. The upper arm portion 20 includes link members 30, 32 and the forearm portion 22 includes link members 34, 36. The link members 30, 32 are pivotally mounted on the cradle 18 and are pivotally connected to the link members 34, 36. The link members 34, 36 are pivotally connected to the guide formation 24. The pivotal connections between the link members 30, 32, 34, 36, the cradle 18, and the guide formation 24 are arranged to constrain the robotic arm 12 to move in a specific manner, specifically with a pivot center 49 is coincident with the port of entry, such that movement of the arm does not excessively effect the surrounding tissue at the port of entry.

Figure 5:
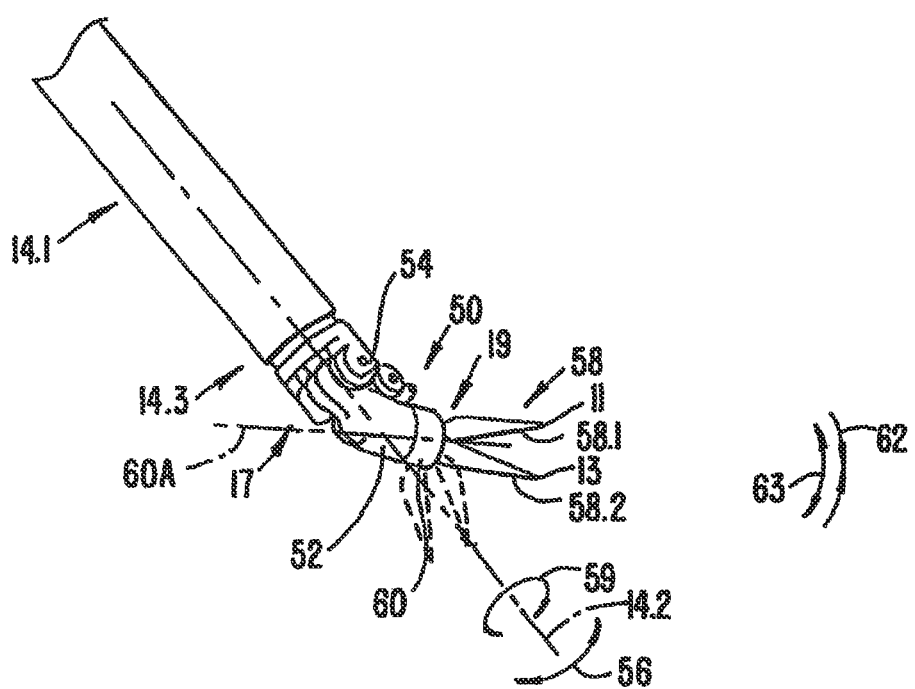
FIG. 5 shows, at an enlarged scale, a wrist member and end effector of the surgical instrument shown in FIG. 3, the wrist member and end effector being movably mounted on a working end of a shaft of the surgical instrument.

Referring now to FIG. 5 of the drawings, the wrist-like mechanism 50 will now be described in greater detail. In FIG. 5, the working end of the shaft 14.1 is indicated at 14.3. The wrist-like mechanism 50 includes a wrist member 52. One end portion of the wrist member 52 is pivotally mounted in a clevis, generally indicated at 17, on the end 14.3 of the shaft 14.1 by means of a pivotal connection 54. The wrist member 52 can pivot in the direction of arrows 56 about the pivotal connection 54. An end effector, generally indicated by reference numeral 58, is pivotally mounted on an opposed end of the wrist member 52. The end effector 58 is in the form of, e.g., a clip applier for anchoring clips during a surgical procedure. Accordingly, the end effector 58 has two parts 58.1, 58.2 together defining a jaw-like arrangement.

It will be appreciated that the end effector can be in the form of any desired surgical tool, e.g., having two members or fingers which pivot relative to each other, such as scissors, pliers for use as needle drivers, or the like. Instead, it can include a single working member, e.g., a scalpel, cautery electrode, or the like. When a tool other than a clip applier is desired during the surgical procedure, the tool 14 is simply removed from its associated arm and replaced with an instrument bearing the desired end effector, e.g., a scissors, or pliers, or the like.

The end effector 58 is pivotally mounted in a clevis, generally indicated by reference numeral 19, on an opposed end of the wrist member 52, by means of a pivotal connection 60. It will be appreciated that free ends 11, 13 of the parts 58.1, 58.2 are angularly displaceable about the pivotal connection 60 toward and away from each other as indicated by arrows 62, 63. It will further be appreciated that the members 58.1, 58.2 can be displaced angularly about the pivotal connection 60 to change the orientation of the end effector 58 as a whole, relative to the wrist member 52. Thus, each part 58.1, 58.2 is angularly displaceable about the pivotal connection 60 independently of the other, so that the end effector 58, as a whole, is angularly displaceable about the pivotal connection 60 as indicated in dashed lines in FIG. 5. Furthermore, the shaft 14.1 is rotatably mounted on the housing 53 for rotation as indicated by the arrows 59. Thus, the end effector 58 has three degrees of freedom of movement relative to the arm 12, namely, rotation about the axis 14.2 as indicated by arrows 59, angular displacement as a whole about the pivot 60 and angular displacement about the pivot 54 as indicated by arrows 56. By moving the end effector within its three degrees of freedom of movement, its orientation relative to the end 14.3 of the shaft 14.1 can selectively be varied. It will be appreciated that movement of the end effector relative to the end 14.3 of the shaft 14.1 is controlled by appropriately positioned actuators, e.g., electrical motors, or the like, which respond to inputs from the associated master control to drive the end effector 58 to a desired orientation as dictated by movement of the master control. Furthermore, appropriately positioned sensors, e.g., encoders, or potentiometers, or the like, are provided to permit the control system of the minimally invasive telesurgical system to determine joint positions as described in greater detail hereinbelow.

Figure 6:
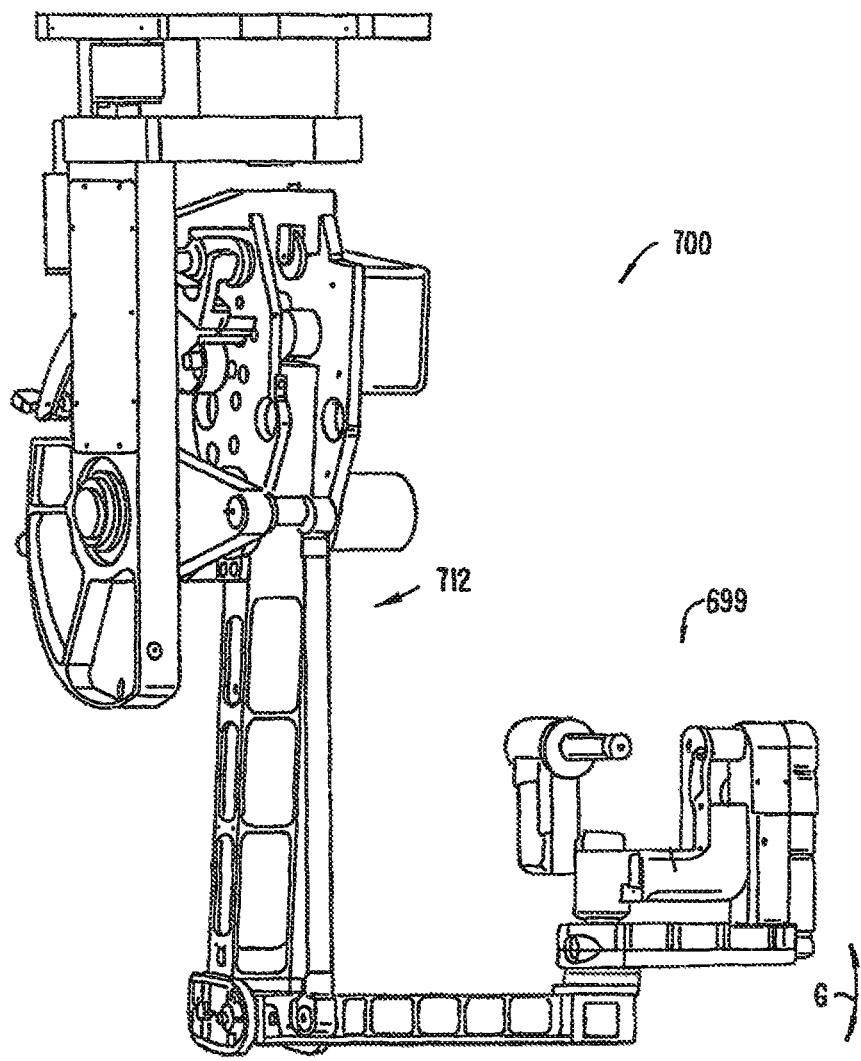
FIG. 6 shows a three-dimensional view of the master control device showing the wrist gimbal mounted on the articulated arm portion.

One of the master controls 700, 700 is indicated in FIG. 6 of the drawings. A hand held part or wrist gimbal of the master control device 700 is generally indicated by reference numeral 699. Part 699 has an articulated arm portion including a plurality of members or links connected together by pivotal connections or joints. The surgeon grips the part 699 by positioning his or her thumb and index finger over a pincher formation. When the pincher formation is squeezed between the thumb and index finger, the fingers or end effector elements of the end effector 58 close. When the thumb and index finger are moved apart the fingers of the end effector 58 move apart in sympathy with the moving apart of the pincher formation. The joints of the part 699 are operatively connected to actuators, e.g., electric motors, or the like, to provide for, e.g., force feedback, gravity compensation, and/or the like, as described in greater detail hereinbelow. Furthermore, appropriately positioned sensors, e.g., encoders, or potentiometers, or the like, are positioned on each joint of the part 699, so as to enable joint positions of the part 699 to be determined by the control system.

The part 699 is typically mounted on an articulated arm 712. The articulated arm 712 includes a plurality of links 714 connected together at pivotal connections or joints 714. It will be appreciated that also the articulated arm 712 has appropriately positioned actuators, e.g., electric motors, or the like, to provide for, e.g., force feedback, gravity compensation, and/or the like. Furthermore, appropriately positioned sensors, e.g., encoders, or potentiometers, or the like, are positioned on the joints so as to enable joint positions of the articulated arm 712 to be determined by the control system.

To move the orientation of the end effector 58 and/or its position along a translational path, the surgeon simply moves the pincher formation to cause the end effector 58 to move to where he wants the end effector 58 to be in the image viewed in the viewer 202. Thus, the end effector position and/or orientation is caused to follow that of the pincher formation. The master control devices 700, 700 are typically mounted on the station 200 through pivotal connections.

The electric motors and sensors associated with the robotic arms 12 and the surgical instruments 14 mounted thereon, and the electric motors and sensors associated with the master control devices 700 are operatively linked in the control system. The control system typically includes at least one processor, typically a plurality of processors, for effecting control between master control device input and responsive robotic arm and surgical instrument output and for effecting control between robotic arm and surgical instrument input and responsive master control output in the case of, e.g., force feedback.

In use, and as schematically indicated in FIG. 7 of the drawings, the surgeon views the surgical site through the viewer 202. The end effector 58 carried on each arm 12 is caused to perform positional and orientational movements in response to movement and action inputs on its associated master controls. The master controls are indicated schematically at 700, 700. It will be appreciated that during a surgical procedure images of the end effectors 58 are captured by the endoscope 304 together with the surgical site and are displayed on the viewer 202 so that the surgeon sees the responsive movements and actions of the end effectors 58 as he or she controls such movements and actions by means of the master control devices 700, 700. The control system is arranged to cause end effector orientational and positional movement as viewed in the image at the viewer 202 to be mapped onto orientational and positional movement of a pincher formation of the master control as will be described in greater detail hereinbelow.

The operation of the control system of the minimally invasive surgical apparatus will now be described in greater detail. In the description which follows, the control system will be described with reference to a single master control 700 and its associated robotic arm 12 and surgical instrument 14. The master control 700 will be referred to simply as "master" and its associated robotic arm 12 and surgical instrument 14 will be referred to simply as "slave."

Figure 8:
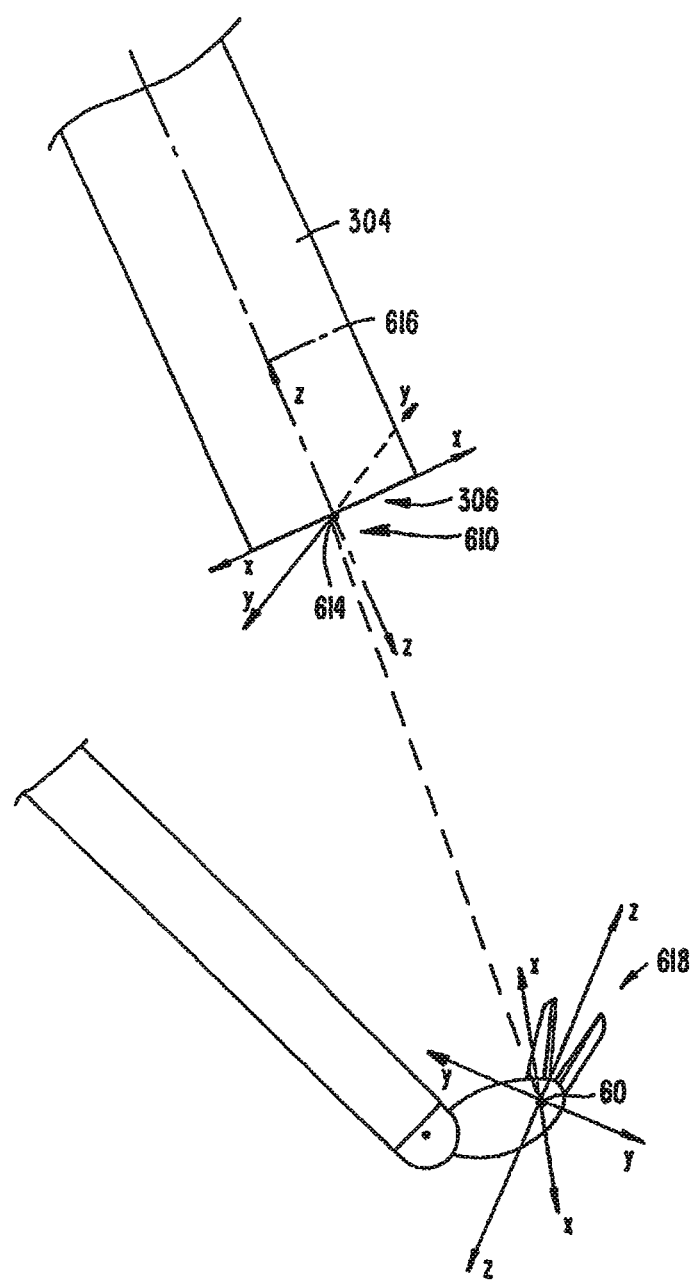
FIG. 8 shows a schematic three-dimensional drawing indicating the position and orientation of an end effector relative to an imaging Cartesian coordinate reference system.

Control between master and slave movement is achieved by comparing master position and orientation in an eye Cartesian coordinate reference system with slave position and orientation in a camera Cartesian coordinate reference system. For ease of understanding and economy of words, the term "Cartesian coordinate reference system" will simply be referred to as "frame" in the rest of this specification. Accordingly, when the master is stationary, the slave position and orientation within the camera frame is compared with the master position and orientation in the eye frame, and should the position and/or orientation of the slave in the camera frame not correspond with the position and/or orientation of the master in the eye frame, the slave is caused to move to a position and/or orientation in the camera frame at which its position and/or orientation in the camera frame does correspond with the position and/or orientation of the master in the eye frame. In FIG. 8, the camera frame is generally indicated by reference numeral 610 and the eye frame is generally indicated by reference numeral 612 in FIG. 9.

When the master is moved into a new position and/or orientation in the eye frame 612, the new master position and/or orientation does not correspond with the previously corresponding slave position and/or orientation in the camera frame 610. The control system then causes the slave to move into a new position and/or orientation in the camera frame 610 at which new position and/or orientation, its position and orientation in the camera frame 610 does correspond with the new position and/or orientation of the master in the eye frame 612.

It will be appreciated that the control system includes at least one, and typically a plurality, of processors which compute new corresponding positions and orientations of the slave in response to master movement input commands on a continual basis determined by the processing cycle rate of the control system. A typical processing cycle rate of the control system under discussion is about 1000 Hz or more, often being about 1300 Hz. Thus, when the master is moved from one position to a next position, the corresponding movement desired by the slave to respond is computed at about 1300 Hz. Naturally, the control system can have any appropriate processing cycle rate depending on the processor or processors used in the control system. All real-time servocycle processing is preferably conducted on a DSP (Digital Signal Processor) chip. DSPs are preferable because of their constant calculation predictability and reproducibility. A Share DSP from Analog Devices, Inc. of Massachusetts is an acceptable example of such a processor for performing the functions described herein.

The camera frame 610 is positioned such that its origin 614 is positioned at the viewing end 306 of the endoscope 304. Conveniently, the z axis of the camera frame 610 extends axially along a viewing axis 616 of the endoscope 304. Although in FIG. 8, the viewing axis 616 is shown in coaxial alignment with a shaft axis of the endoscope 304, it is to be appreciated that the viewing axis 616 can be angled relative thereto. Thus, the endoscope can be in the form of an angled scope. Naturally, the x and y axes are positioned in a plane perpendicular to the z axis. The endoscope is typically angularly displaceable about its shaft axis. The x, y and z axes are fixed relative to the viewing axis of the endoscope 304 so as to displace angularly about the shaft axis in sympathy with angular displacement of the endoscope 304 about its shaft axis.

To enable the control system to determine slave position and orientation, a frame is defined on or attached to the end effector 58. This frame is referred to as an end effector frame or slave tip frame, in the rest of this specification, and is generally indicated by reference numeral 618. The end effector frame 618 has its origin at the pivotal connection 60. Conveniently, one of the axes e.g. the z axis, of the frame 618 is defined to extend along an axis of symmetry, or the like, of the end effector 58. Naturally, the x and y axes then extend perpendicularly to the z axis. It will appreciated that the orientation of the slave is then defined by the orientation of the frame 618 having its origin at the pivotal connection 60, relative to the camera frame 610. Similarly, the position of the slave is then defined by the position of the origin of the frame at 60 relative to the camera frame 610.

Figure 9:
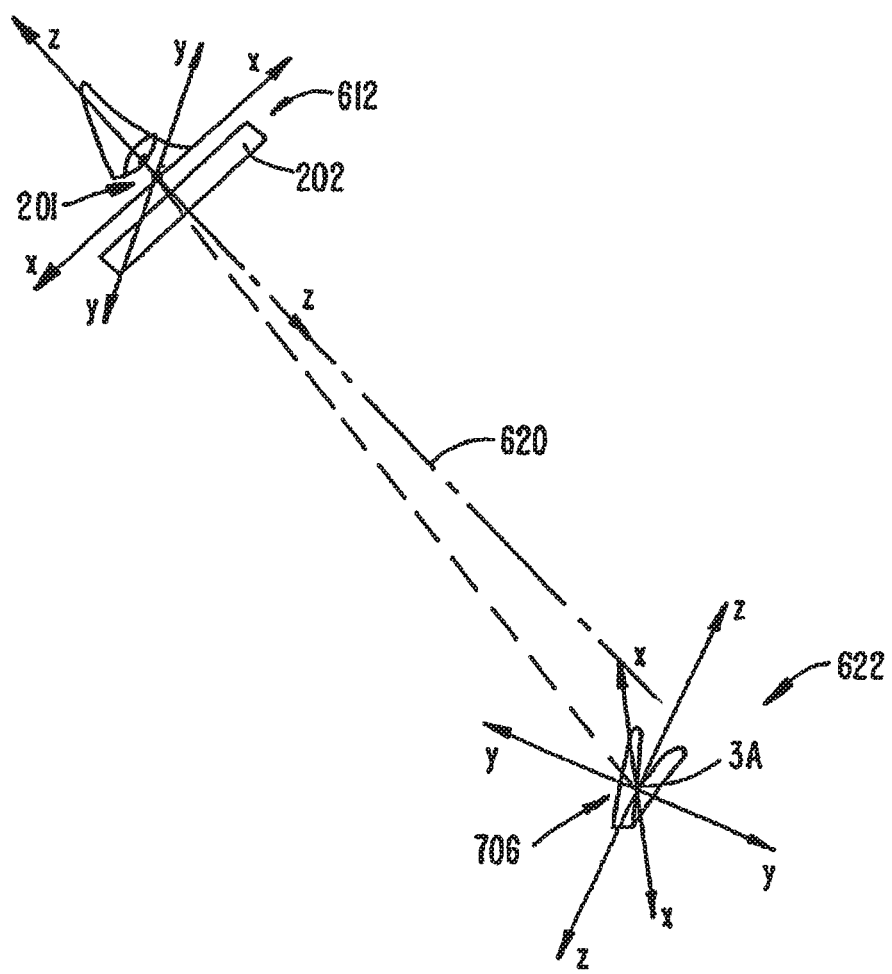
FIG. 9 shows a schematic three-dimensional drawing indicating the position and orientation of a pincer formation of the master control device relative to an eye Cartesian coordinate reference system.

Referring now to FIG. 9 of the drawings, the eye frame 612 is chosen such that its origin corresponds with a position 201 where the surgeon's eyes are normally located when he or she is viewing the surgical site at the viewer 202. The z axis extends along a line of sight of the surgeon, indicated by axis 620, when viewing the surgical site through the viewer 202. Naturally, the x and y axes extend perpendicularly from the z axis at the origin 201. Conveniently, the y axis is chosen to extend generally vertically relative to the viewer 202 and the x axis is chosen to extend generally horizontally relative to the viewer 202.

To enable the control system to determine master position and orientation within the viewer frame 612, a point on the master is chosen which defines an origin of a master or master tip frame, indicated by reference numeral 622. This point is chosen at a point of intersection indicated by reference numeral 3A between axes of rotation 1 and 3 of the master. Conveniently, the z axis of the master frame 622 on the master extends along an axis of symmetry of the pincher formation 706 which extends coaxially along the rotational axis 1. The x and y axes then extend perpendicularly from the axis of symmetry 1 at the origin 3A. Accordingly, orientation of the master within the eye frame 612 is defined by the orientation of the master frame 622 relative to the eye frame 612. The position of the master in the eye frame 612 is defined by the position of the origin 3A relative to the eye frame 612.

Figure 10:
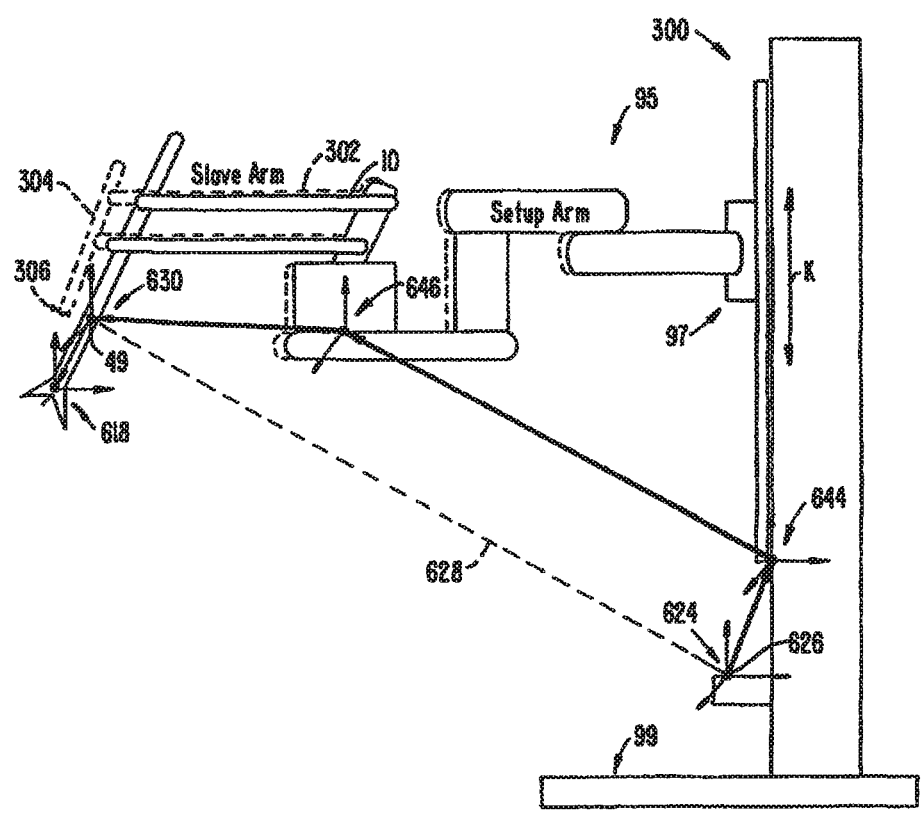
FIG. 10 shows a schematic side view of part of the surgical station of the minimally invasive surgical apparatus indicating the location of Cartesian reference coordinate systems used to determine the position and orientation of an end effector relative an image capturing device.

How the position and orientation of the slave within the camera frame 610 is determined by the control system will now be described with reference to FIG. 10 of the drawings. FIG. 10 shows a schematic diagram of one of the robotic arm 12 and surgical instrument 14 assemblies mounted on the cart 300. When used for neurosurgery, cardiology, and/or orthopedic surgery, the linkages of the robotic arm and its associated instrument may be altered or tailored for positioning and moving a flexible catheter body, an orthopedic probe, or the like. However, before commencing with a description of FIG. 10, it is appropriate to describe certain previously mentioned aspects of the surgical station 300 which impact on the determination of the orientation and position of the slave relative to the camera frame 610.

In use, when it is desired to perform a surgical procedure by means of the minimally invasive surgical apparatus, the surgical station 300 is moved into close proximity to a patient requiring the surgical procedure. The patient is normally supported on a surface such as an operating table, or the like. To make allowance for support surfaces of varying height, and to make allowance for different positions of the surgical station 300 relative to the surgical site at which the surgical procedure is to be performed, the surgical station 300 is provided with the ability to have varying initial setup configurations. Accordingly, the robotic arms 12, 12, and the endoscope arm 302 are mounted on the carriage 97 which is height-wise adjustable, as indicated by arrows K, relative to the base 99 of the cart 300, as can best be seen in FIGS. 2 and 10 of the drawings. Furthermore, the robotic arms 12, 12 and the endoscope arm 302 are mounted on the carriage 97 by means of the setup joint arms 95. Thus, the lateral position and orientation of the arms 12, 12, 302 can be selected by moving the setup joint arms 95. Thus, at the commencement of the surgical procedure, the cart 300 is moved into the position in close proximity to the patient, an appropriate height of the carriage 97 is selected by moving it to an appropriate height relative to the base 99 and the surgical instruments 14 are moved relative to the carriage 97 so as to introduce the shafts of the instruments 14 and the endoscope 304 through the ports of entry and into positions in which the end effectors 58 and the viewing end 306 of the endoscope 304 are appropriately positioned at the surgical site and the fulcrums are coincident with the ports of entry. Once the height and positions are selected, the carriage 97 is locked at its appropriate height and the setup joint arms 95 are locked in their positions and orientations. Normally, throughout the surgical procedure, the carriage 97 is maintained at the selected height and similarly the setup joint arms 95 are maintained in their selected positions. However, if desired, either the endoscope or one or both of the instruments can be introduced through other ports of entry during the surgical procedure.

Returning now to FIG. 10, the determination by the control system of the position and orientation of the slave within the camera frame 610 will now be described. It will be appreciated that this is achieved by means of one or more processors having a specific processing cycle rate. Thus, where appropriate, whenever position and orientation are referred to in this specification, it should be borne in mind that a corresponding velocity is also readily determined. The control system determines the position and orientation of the slave within the camera frame 610 by determining the position and orientation of the slave relative to a cart frame 624 and by determining the orientation and position of the endoscope 304 with reference to the same cart frame 624. The cart frame 624 has an origin indicated by reference numeral 626 in FIG. 10.

To determine the position and orientation of the slave relative to the cart frame 624, the position of a fulcrum frame 630 having its origin at the fulcrum 49 is determined within the cart frame 624 as indicated by the arrow 628 in dashed lines. It will be appreciated that the position of the fulcrum 49 normally remains at the same location, coincident with a port of entry into the surgical site, throughout the surgical procedure. The position of the end effector frame 618 on the slave, having its origin at the pivotal connection 60, is then determined relative to the fulcrum frame 630 and the orientation of the end effector frame 618 on the slave is also determined relative to the fulcrum frame 630. The position and orientation of the end effector frame 618 relative to the cart frame is then determined by means of routine calculation using trigonometric relationships.

It will be appreciated that the robotic arm 302 of the endoscope 304 is constrained to move in similar fashion to the robotic arm 10. Thus, the endoscope 304 when positioned with its viewing end 306 directed at the surgical site, also defines a fulcrum coincident with its associated port of entry into the surgical site. The endoscope arm 302 can be driven to cause the endoscope 304 to move into a different position during a surgical procedure, to enable the surgeon to view the surgical site from a different position in the course of performing the surgical procedure. It will be appreciated that movement of the viewing end 306 of the endoscope 304 is performed by varying the orientation of the endoscope 304 relative to its pivot center or fulcrum. The position and orientation of the camera frame 610 within the cart frame 624 is determined in similar fashion to the position and orientation of the slave within the cart frame 624. When the position and orientation of the camera frame 610 relative to the cart frame 624, and the position and orientation of the slave relative to the cart frame 624 have been determined in this manner, the position and the orientation of the slave relative to the camera frame 610 is readily determinable through routine calculation using trigonometric relationships.

Figure 11:
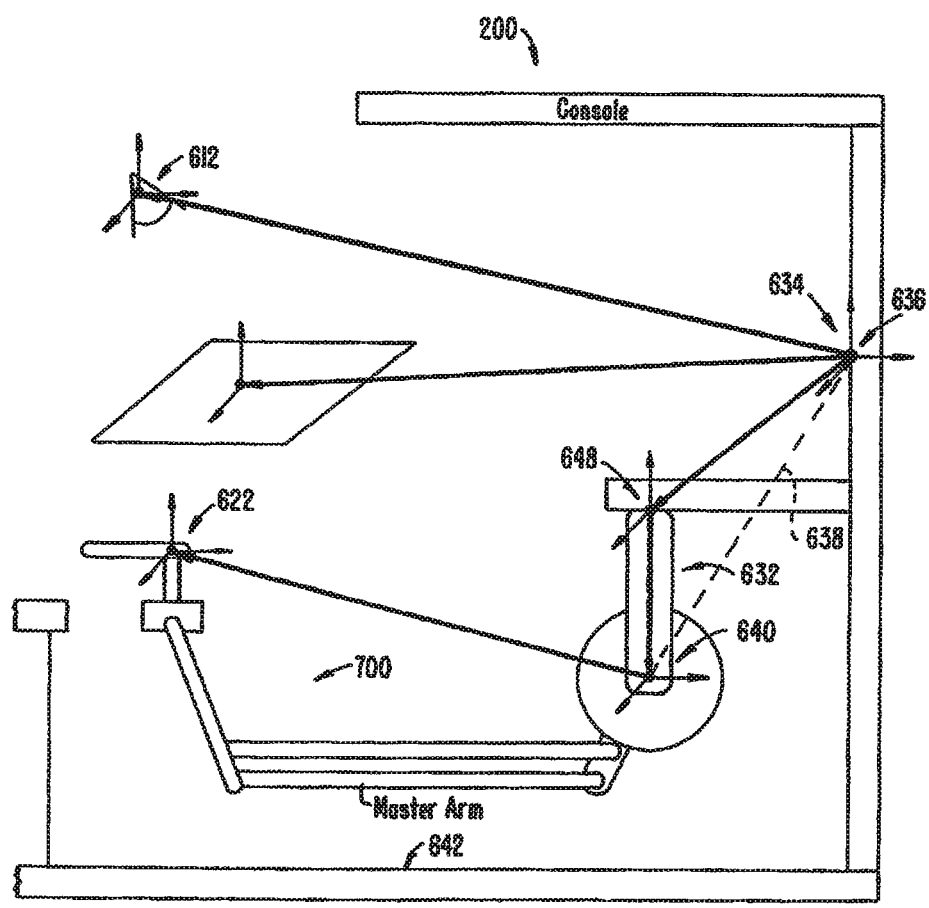
FIG. 11 shows a schematic side view of part of the operator station of the minimally invasive surgical apparatus indicating the location of Cartesian reference coordinate systems used by the control systems of the minimally invasive surgical apparatus to determine the position and orientation of the input device relative to an eye of the system operator.

How the position and orientation of the master within the viewer frame 612 is determined by the control system will now be described with reference to FIG. 11 of the drawings. FIG. 11 shows a schematic diagram of one of the master controls 700 at the operator station 200.

The operator station 200 optionally also includes setup joint arms, as indicated at 632, to enable the general location of the masters 700, 700 to be varied to suit the surgeon. Thus, the general position of the masters 700, 700 can be selectively varied to bring the masters 700, 700 into a general position at which they are comfortably positioned for the surgeon. When the masters 700, 700 are thus comfortably positioned, the setup joint arms 632 are locked in position and are normally maintained in that position throughout the surgical procedure.

To determine the position and orientation of the master 700, as indicated in FIG. 11, within the eye frame 612, the position and orientation of the eye frame 612 relative to a surgeon's station frame 634, and the position and orientation of the master 700 relative to the surgeon's frame 634 is determined. The surgeon's station frame 634 has its origin at a location which is normally stationary during the surgical procedure, and is indicated at 636.

To determine the position and orientation of the master 700 relative to the station frame 634, a position of a master setup frame 640 at an end of the setup joint arms 632 on which the master 700 is mounted, relative to the station frame 636, is determined, as indicated by the arrow 638 in dashed lines. The position and orientation of the master frame 622 on the master 700 having its origin at 3A is then determined relative to the master setup frame 640. In this manner, the position and orientation of the master frame 622 relative to the frame 634 can be determined by means of routine calculation using trigonometric relationships. The position and orientation of the eye frame 612 relative to the station frame 634 is determined in similar fashion. It will be appreciated that the position of the viewer 202 relative to the rest of the surgeon's console 200 can selectively be varied to suit the surgeon. The position and orientation of the master frame 622 relative to the eye frame 612 can then be determined from the position and orientation of the master frame 622 and the eye frame 612 relative to the surgeon station frame 634 by means of routine calculation using trigonometric relationships.

In the manner described above, the control system of the minimally invasive surgical apparatus determines the position and orientation of the end effector 58 by means of the end effector frame 618 in the camera frame 610, and, likewise, determines the position and orientation of the master by means of the master frame 622 relative to the eye frame 612.

As mentioned, the surgeon grips the master by locating his or her thumb and index finger over the pincher formation 706. When the surgeon's thumb and index finger are located on the pincher formation, the point of intersection 3A is positioned inwardly of the thumb and index finger tips. The master frame having its origin at 3A is effectively mapped onto the end effector frame 618, having its origin at the pivotal connection 60 of the end effector 58 as viewed by the surgeon in the viewer 202. Thus, when performing the surgical procedure, and the surgeon manipulates the position and orientation of the pincher formation 706 to cause the position and orientation of the end effector 58 to follow, it appears to the surgeon that his or her thumb and index finger are mapped onto the fingers of the end effector 58 and that the pivotal connection 60 of the end effector 58 corresponds with a virtual pivot point of the surgeon's thumb and index finger inwardly from the tips of the thumb and index finger.

Accordingly, as the surgical procedure is being performed the position and orientation of the fingers of the end effector tracks orientation and position changes of the surgeon's thumb and index finger in a natural intuitive or superimposed fashion. Furthermore, actuation of the end effector 58, namely causing the end effector fingers selectively to open and close, corresponds intuitively to the opening and closing of the surgeon's thumb and index finger. Thus, actuation of the end effector 58 as viewed in the viewer 302 is performed by the surgeon in a natural intuitive manner, since the pivot point 60 of the end effector 58 is appropriately mapped onto a virtual pivot point between the surgeon's thumb and index finger.

Referring again to FIG. 10 of the drawings, the cart frame is chosen at 624. It will be appreciated that determining the position of the fulcrum frame 630 relative to the cart frame 624 is achieved through appropriately positioned sensors, such as potentiometers, encoders, or the like. Conveniently, the fulcrum frame position 630 relative to the cart frame 624 is determined through two intermediate frames. One of the frames is a carriage guide frame 644 which has its origin at a convenient location on a guide along which the carriage 97 is guided. The other frame, an arm platform frame indicated at 646 is positioned at an end of the setup joint arm 95 on which the robotic arm 12 is mounted. Thus, when slave position and orientation is determined relative to the cart frame 624, the carriage guide frame 644 position relative to the cart frame 624 is determined, then the platform frame 646 position relative to the carriage guide frame 644, then the fulcrum frame 630 relative to the platform frame 646, and then the slave orientation and position relative to the fulcrum frame 630, thereby to determine the slave position and orientation relative to the cart frame 624. It will be appreciated that the slave position and orientation relative to the cart frame 624 is determined in this manner for each arm 10 and in similar fashion for the camera frame 610, through its arm 302, relative to the cart frame 624.

Referring to FIG. 11, the position and orientation of the master control is determined by determining the position of a base frame 648 relative to the surgeon's station frame 634, then determining the position of the platform frame 640 relative to the base frame 648, and then determining master position and orientation relative to the platform frame 640. The position and orientation of the master frame 622 relative to the surgeon's station frame 634 is then readily determined through routine calculation using trigonometric relationships. It will be appreciated that the position and orientation of the other master frame relative to the surgeon console frame 634 is determined in a similar fashion.

Figure 12:
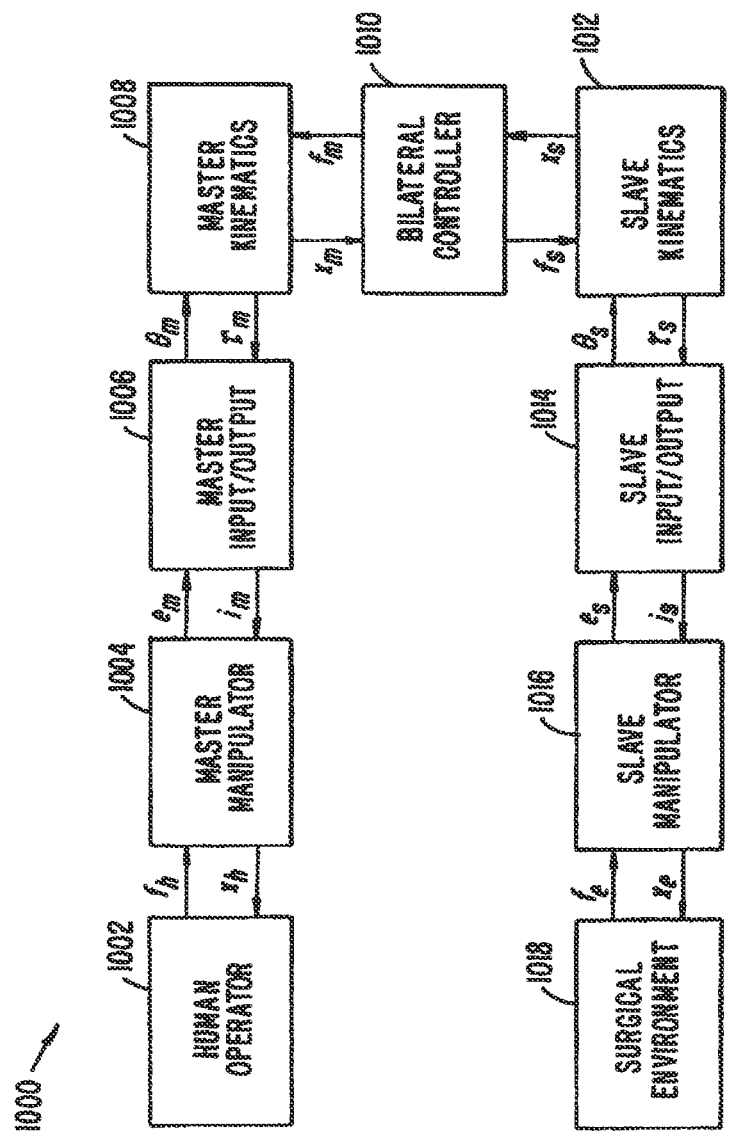
FIG. 12 schematically illustrates a high level control architecture model of a master/slave surgical robotic system.

FIG. 12 schematically illustrates a high level control architecture for a master/slave robotic system 1000. Beginning at the operator input, a surgeon 1002 moves an input device of a master manipulator 1004 by applying manual or human forces $f_h$ against the input device. Encoders of master manipulator 1004 generate master encoder signals $e_m$ which are interpreted by a master input/output processor 1006 to determine the master joint positions $\theta_m$. The master joint positions are used to generate Cartesian positions of the input device of the master $x_m$ using a master kinematics model 1008.

Starting now with the input from the surgical environment 1018, the tissue structures in the surgical workspace will impose forces $f_e$ against a surgical end effector (and possibly against other elements of the tool and/or manipulator). Environmental forces $f_e$ from the surgical environment 1018 alter position of the slave 1016, thereby altering slave encoder values $e_s$ transmitted to the slave input/output processor 1014. Slave input/output processor 1014 interprets the slave encoder values to determine joint positions $\theta_s$, which are then used to generate Cartesian slave position signals $x_s$ according to the slave kinematics processing block 1012.

The master and slave Cartesian positions $x_m$, $x_s$ are input into bilateral controller 1010, which uses these inputs to generate the desired Cartesian forces to be applied by the slave $f_s$ so that the surgeon can manipulate the salve as desired to perform a surgical procedure. Additionally, bilateral controller 1010 uses the Cartesian master and slave positions $x_m$, $x_s$ to generate the desired Cartesian forces to be applied by the master $f_m$ so as to provide force feedback to the surgeon.

In general, bilateral controller 1010 will generate the slave and master forces $f_s$, $f_m$ by mapping the Cartesian position of the master in the master controller workspace with the Cartesian position of the end effector in the surgical workspace according to a transformation. Preferably, the control system 1000 will derive the transformation in response to state variable signals provided from the imaging system on that an image of the end effector in a display appears substantially connected to the input device. These state variables will generally indicate the Cartesian position of the field of view from the image capture device, as supplied by the slave manipulators supporting the image capture device. Hence, coupling of the image capture manipulator and slave end effector manipulator is beneficial for deriving this transformation. Clearly, bilateral controller 1010 may be used to control more than one slave arm, and/or may be provided with additional inputs.

Based generally on the difference in position between the master and the slave in the mapped workspace, bilateral controller 1010 generates Cartesian slave force $f_s$ to urge the slave to follow the position of the master. The slave kinematics 1012 are used to interpret the Cartesian slave forces $f_s$ to generate joint torques of the slave $\tau_s$ which will result in the desired forces at the end effector. Slave input/output processor 1014 uses these joint torques to calculate slave motor currents $i_s$, which reposition the slave $x_e$ within the surgical worksite.

The desired feedback forces from bilateral controller are similarly interpreted from Cartesian force on the master $f_m$ based on the master kinematics 1008 to generate master joint torques $\tau_s$. The master joint torques are interpreted by the master input/output controller 1006 to provide master motor current $i_m$ to the master manipulator 1004, which changes the position of the hand held input device $x_h$ in the surgeon's hand.

It will be recognized that the control system 1000 illustrated in FIG. 12 is a simplification. For example, the surgeon does not only apply forces against the master input device, but also moves the handle within the master workspace. Similarly, the motor current supplied to the motors of the master manipulator may not result in movement if the surgeon maintains the position of the master controller. Nonetheless, the motor currents do result in tactile force feedback to the surgeon based on the forces applied to the slave by the surgical environment. Additionally, while Cartesian coordinate mapping is preferred, the use of spherical, cylindrical, or other reference frames may provide at least some of the advantages of the invention.

Figure 13:
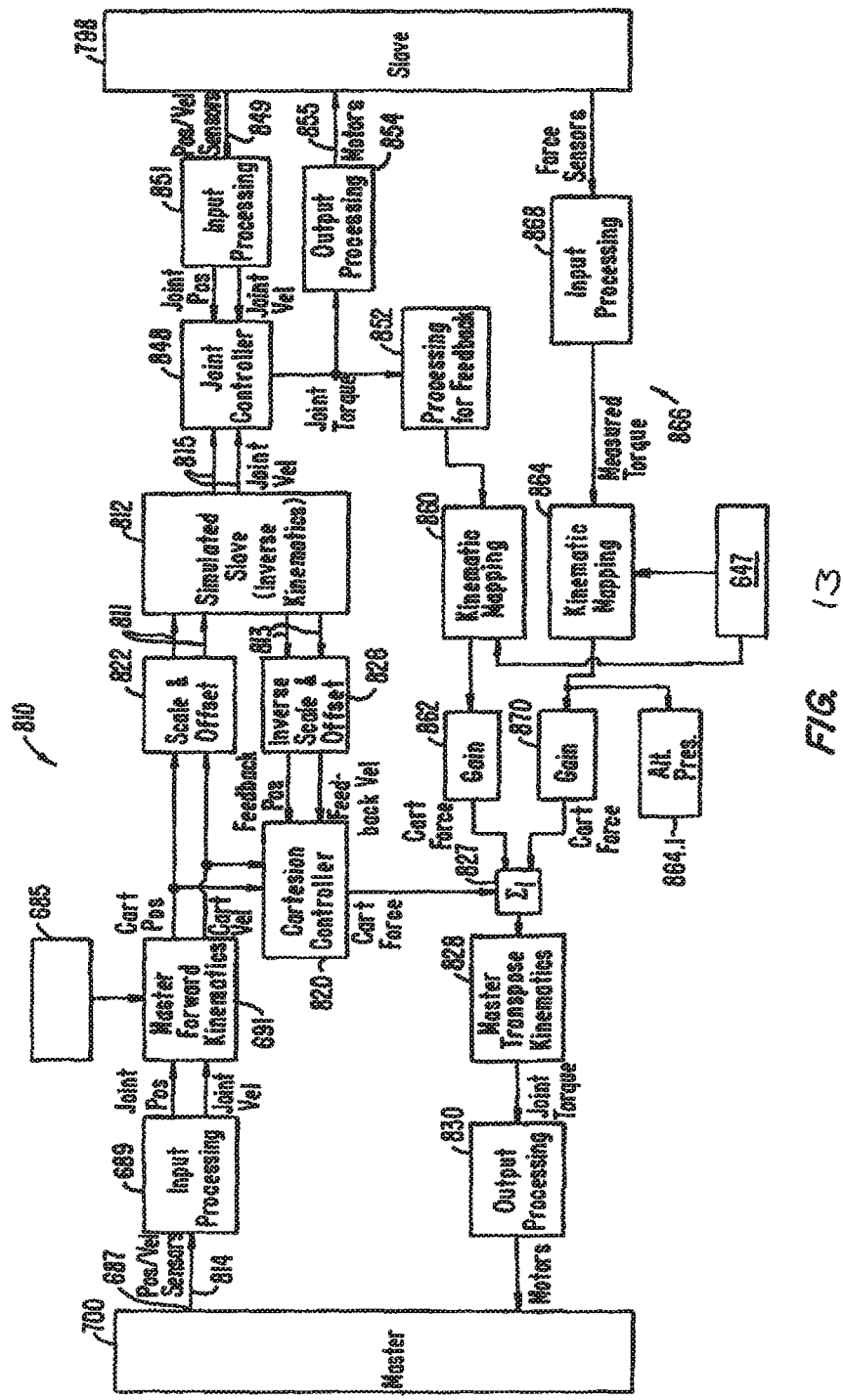
FIG. 13 shows a block diagram representing control steps followed by the control system of the minimally invasive surgical apparatus in effecting control between input device positional and orientational movement and end effector positional and orientational movement.
Figure 14:
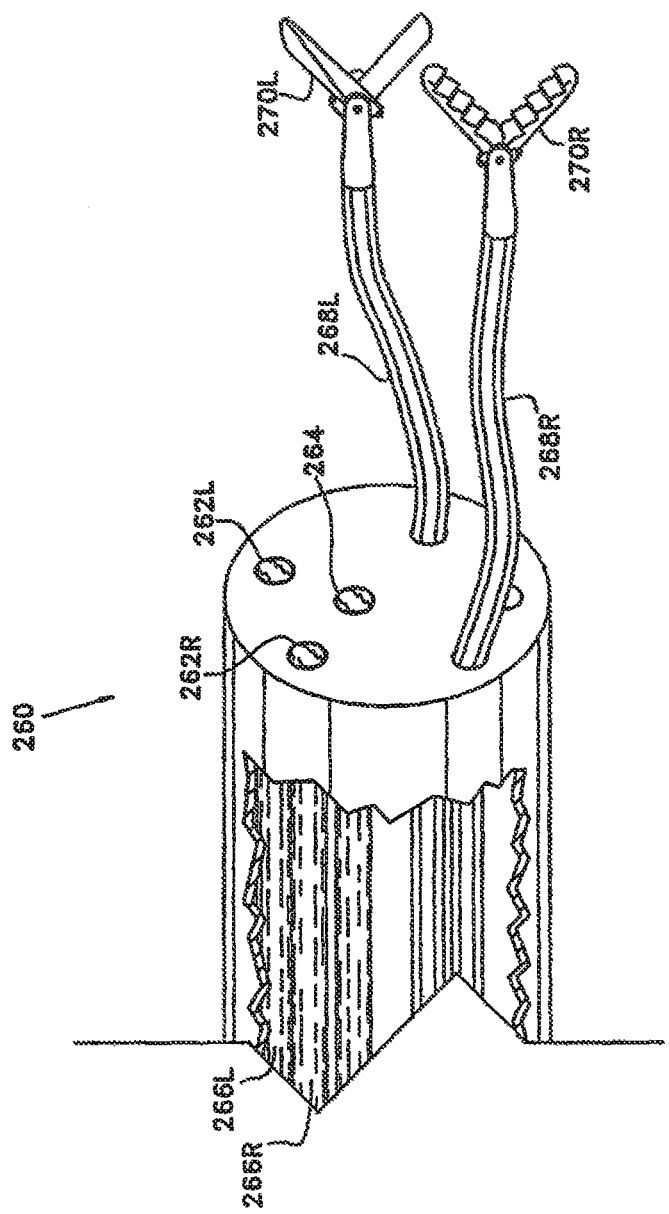
FIG. 14 shows a fragmentary portion of the insertion portion of an endoscope for use with the present invention.

The control system, generally indicated by reference numeral 810, will now be described in greater detail with reference to FIG. 13 of the drawings, in which like reference numerals are used to designate similar parts or aspects, unless otherwise stated.

As mentioned earlier, the master control 700 has sensors, e.g., encoders, or potentiometers, or the like, associated therewith to enable the control system 810 to determine the position of the master control 700 in joint space as it is moved from one position to a next position on a continual basis during the course of performing a surgical procedure. In FIG. 13, signals from these positional sensors are indicated by arrow 814. Positional readings measured by the sensors at 687 are read by the processor. It will be appreciated that since the master control 700 includes a plurality of joints connecting one arm member thereof to the next, sufficient positional sensors are provided on the master 700 to enable the angular position of each arm member relative to the arm member to which it is joined to be determined thereby to enable the position and orientation of the master frame 622 on the master to be determined. As the angular positions of one arm member relative to the arm member to which it is joined is read cyclically by the processor 689 in response to movements induced on the master control 700 by the surgeon, the angular positions are continuously changing. The processor at 689 reads these angular positions and computes the rate at which these angular positions are changing. Thus, the processor 689 reads angular positions and computes the rate of angular change, or joint velocity, on a continual basis corresponding to the system processing cycle time, i.e., 1300 Hz. Joint position and joint velocity commands thus computed at 689 are then input to the Forward Kinematics (FKIN) controller at 691, as already described hereinabove.

At the FKIN controller 691, the positions and velocities in joint space are transformed into corresponding positions and velocities in Cartesian space, relative to the eye frame 612. The FKIN controller 691 is a processor which typically employs a Jacobian (J) matrix to accomplish this. It will be appreciated that the Jacobian matrix transforms angular positions and velocities into corresponding positions and velocities in Cartesian space by means of conventional trigonometric relationships. Thus, corresponding positions and velocities in Cartesian space, or Cartesian velocity and position commands, are computed by the FKIN controller 691 which correspond to Cartesian position and velocity changes of the master frame 622 in the eye frame 612.

The velocity and the position in Cartesian space is input into a Cartesian controller, indicated at 820, and into a motion scale and offset converter, indicated at 822.

The minimally invasive surgical apparatus provides for a motion scale change between master control input movement and responsive slave output movement. Thus, a motion scale can be selected where, for example, a 1-inch movement of the master control 700 is transformed into a corresponding responsive ⅓-inch movement on the slave. At the motion scale and offset step 822, the Cartesian position and velocity values are scaled in accordance with the scale selected to perform the surgical procedure. Naturally, if a motion scale of 1:1 has been selected, no change in motion scale is effected at 822. Similarly, offsets are taken into account which determine the corresponding position and/or orientation of the end effector frame 618 in the camera frame 610 relative to the position and orientation of the master frame 622 in the eye frame 612.

After a motion scale and offset step is performed at 822, a resultant desired slave position and desired slave velocity in Cartesian space is input to a simulated or virtual domain at 812, as indicated by arrows 811. It will be appreciated that the labeling of the block 812 as a simulated or virtual domain is for identification only. Accordingly, the simulated control described hereinbelow is performed by elements outside the block 812 also.

The simulated domain 812 will be described in greater detail hereinbelow. However, the steps imposed on the desired slave velocity and position in the virtual domain 812 will now be described broadly for ease of understanding of the description which follows. A current slave position and velocity is continually monitored in the virtual or simulated domain 812. The desired slave position and velocity is compared with the current slave position and velocity. Should the desired slave position and/or velocity as input from 822 not cause transgression of limitations, e.g., velocity and/or position and/or singularity, and/or the like, as set in the virtual domain 812, a similar Cartesian slave velocity and position is output from the virtual domain 812 and input into an inverse scale and offset converter as indicated at 826. The similar velocity and position output in Cartesian space from the virtual domain 812 is indicated by arrows 813 and corresponds with actual commands in joint space output from the virtual domain 812 as indicated by arrows 815 as will be described in greater detail hereinbelow. From the inverse scale and offset converter 826, which performs the scale and offset step of 822 in reverse, the reverted Cartesian position and velocity is input into the Cartesian controller at 820. At the Cartesian controller 820, the original Cartesian position and velocities as output from the FKIN controller 691 is compared with the Cartesian position and velocity input from the simulated domain 812. If no limitations were transgressed in the simulated domain 812 the velocity and position values input from the FKIN controller 691 would be the same as the velocity and position values input from the simulated domain 812. In such a case, a zero error signal is generated by the Cartesian controller 820.

In the event that the desired Cartesian slave position and velocity input at 811 would transgress one or more set limitations, the desired values are restricted to stay within the bounds of the limitations. Consequently, the Cartesian velocity and position forwarded from the simulated domain 812 to the Cartesian controller 820 would then not be the same as the values from the FKIN controller 691. In such a case, when the values are compared by the Cartesian controller 820, an error signal is generated.

Assuming that a zero error is generated at the Cartesian controller 820 no signal is passed from the Cartesian controller or converter 820. In the case that an error signal is generated the signal is passed through a summation junction 827 to a master transpose kinematics controller 828.

The error signal is typically used to calculate a Cartesian force. The Cartesian force is typically calculated, by way of example, in accordance with the following formula:

$$F_{CART} = K(\Delta x) + B(\Delta x)$$

where K is a spring constant, B is a damping constant, $\Delta x$ is the difference between the Cartesian velocity inputs to the Cartesian controller 820 and $\Delta x$ is the difference between the Cartesian position inputs to the Cartesian controller 820. It will be appreciated that for an orientational error, a corresponding torque in Cartesian space is determined in accordance with conventional methods.

The Cartesian force corresponds to an amount by which the desired slave position and/or velocity extends beyond the limitations imposed in the simulated domain 812. The Cartesian force, which could result from a velocity limitation, a positional limitation, and/or a singularity limitation, as described in greater detail below, is then converted into a corresponding torque signal by means of the master transpose kinematics controller 828 which typically includes a processor employing a Jacobian Transpose ($J^T$) matrix and kinematic relationships to convert the Cartesian force to a corresponding torque in joint space. The torque thus determined is then input to a processor at 830 whereby appropriate electrical currents to the motors associated with the master 700 are computed and supplied to the motors. These torques are then applied on the motors operatively associated with the master control 700. The effect of this is that the surgeon experiences a resistance on the master control to either move it at the rate at which he or she is urging the master control to move, or to move it into the position into which he or she is urging the master control to move. The resistance to movement on the master control is due to the torque on the motors operatively associated therewith. Accordingly, the higher the force applied on the master control to urge the master control to move to a position beyond the imposed limitation, the higher the magnitude of the error signal and the higher an opposing torque on the motors resisting displacement of the master control in the direction of that force. Similarly, the higher the velocity imposed on the master beyond the velocity limitation, the higher the error signal and the higher the opposing torque on the motors associated with the master.

Referring once again to FIG. 13 of the drawings, the slave joint velocity and position signal is passed from the simulated domain 812 to a joint controller 848. At the joint controller 848, the resultant joint velocity and position signal is compared with the current joint position and velocity. The current joint position and velocity is derived through the sensors on the slave as indicated at 849 after having been processed at an input processor 851 to yield slave current position and velocity in joint space.

The joint controller 848 computes the torques desired on the slave motors to cause the slave to follow the resultant joint position and velocity signal taking its current joint position and velocity into account. The joint torques so determined are then routed to a feedback processor at 852 and to an output processor at 854.

The joint torques are typically computed, by way of example, by means of the following formula:

$$T = K(\Delta\theta) + B(\Delta\dot{\theta})$$

where K is a spring constant, B is a damping constant, $\Delta\dot{\theta}$ is the difference between the joint velocity inputs to the joint controller 851, and $\Delta\theta$ is the difference between the joint position inputs to the joint controller 851.

The output processor 854 determines the electrical currents to be supplied to the motors associated with the slave to yield the commanded torques and causes the currents to be supplied to the motors as indicated by arrow 855.

From the feedback processor 852 force feedback is supplied to the master. As mentioned earlier, force feedback is provided on the master 700 whenever a limitation is induced in the simulated domain 812. Through the feedback processor 852 force feedback is provided directly from the slave 798, in other words, not through a virtual or simulated domain but through direct slave movement. This will be described in greater detail hereinbelow.

As mentioned earlier, the slave indicated at 798 is provided with a plurality of sensors. These sensors are typically operatively connected to pivotal joints on the robotic arm 10 and on the instrument 14.

These sensors are operatively linked to the processor at 851. It will be appreciated that these sensors determine current slave position. Should the slave 798 be subjected to an external force great enough to induce reactive movement on the slave 798, the sensors will naturally detect such movement. Such an external force could originate from a variety of sources such as when the robotic arm 10 is accidentally knocked, or knocks into the other robotic arm 10 or the endoscope arm 302, or the like. As mentioned, the joint controller 848 computes torques desired to cause the slave 798 to follow the master 700. An external force on the slave 798 which causes its current position to vary also causes the desired slave movement to follow the master to vary. Thus a compounded joint torque is generated by the joint controller 848, which torque includes the torque desired to move the slave to follow the master and the torque desired to compensate for the reactive motion induced on the slave by the external force. The torque generated by the joint controller 848 is routed to the feedback processor at 852, as already mentioned. The feedback processor 852 analyzes the torque signal from the joint controller 848 and accentuates that part of the torque signal resulting from the extraneous force on the slave 798. The part of the torque signal accentuated can be chosen depending on requirements. In this case, only the part of the torque signal relating to the robotic arm 12, 12, 302 joints are accentuated. The torque signal, after having been processed in this way is routed to a kinematic mapping block 860 from which a corresponding Cartesian force is determined. At the kinematic block 860, the information determining slave fulcrum position relative to the camera frame is input from 647 as indicated. Thus, the Cartesian force is readily determined relative to the camera frame. This Cartesian force is then passed through again step at 862 appropriately to vary the magnitude of the Cartesian force. The resultant force in Cartesian space is then passed to the summation junction at 827 and is then communicated to the master control 700 as described earlier.

Reference numeral 866 generally indicates another direct force feedback path of the control system 810, whereby direct force feedback is supplied to the master control 700. The path 866 includes one or more sensors which are not necessarily operatively connected to slave joints. These sensors can typically be in the form of force or pressure sensors appropriately positioned on the surgical instrument 14, typically on the end effector 58. Thus, should the end effector 58 contact an extraneous body, such as body tissue at the surgical site, it generates a corresponding signal proportionate to the force of contact. This signal is processed by a processor at 868 to yield a corresponding torque. This torque is passed to a kinematic mapping block 864, together with information from 647 to yield a corresponding Cartesian force relative to the camera frame. From 864, the resultant force is passed through a gain block at 870 and then forwarded to the summation junction 827. Feedback is imparted on the master control 700 by means of torque supplied to the motors operatively associated with the master control 700 as described earlier. It will be appreciated that this can be achieved by means of any appropriate sensors such as current sensors, pressure sensors, accelerometers, proximity detecting sensors, or the like. In some embodiments, resultant forces from kinematic mapping 864 may be transmitted to an alternative presentation block 864.1 so as to indicate the applied forces in an alternative format to the surgeon.

Reference now is made to HG. 14 wherein a distal end portion, or tip, 260 of the insertion section of a flexible instrument or endoscope is shown. The insertion end of the instrument includes a pair of spaced viewing windows 262R and 262L and an illumination source 264 for viewing and illuminating a workspace to be observed. Light received at the windows is focused by objective lens means, not shown, and transmitted through fiber-optic bundles to a pair of cameras at the operating end of the instrument, not shown. The camera outputs are converted to a three-dimensional image of the workspace which image is located adjacent hand-operated means at the operator's station, now shown. Right and left steerable catheters 268R and 268L pass through accessory channels in the endoscope body, which catheters are adapted for extension from the distal end portion, as illustrated. End effectors 270R and 270L are provided at the ends of the catheters which may comprise conventional endoscopic instruments. Force sensors, not shown, also are inserted through the endoscope channels. Steerable catheters which include control wires for controlling bending of the catheters and operation of an end effector suitable for use with this invention are well know. Control motors for operation of the control wires are provided at the operating end of the endoscope, which motors are included in a servomechanism of a type described above for operation of the steerable catheters and associated end effectors from a remote operator's station. As with the other embodiments, the interfacing computer in the servomechanism system remaps the operator's hand motion into the coordinate system of the end effectors, and images of the end effectors are viewable adjacent the hand-operated controllers in a manner described above. Flexible catheter-based instruments and probes of different types may be employed in this embodiment of the invention.

Figure 15:
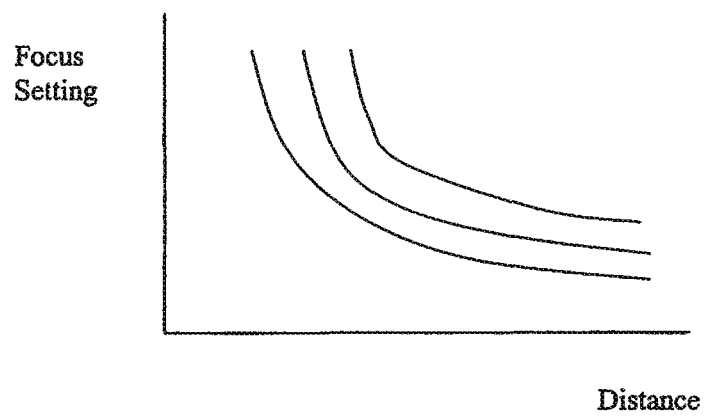
FIG. 15 is a schematic representation of a correlation between a focus setting of an image capture device and a separation distance between the image capture device and the focus point.

In determining, establishing, and maintaining a desired focus point for the endoscope or other image capture device, the controller or processor of the telesurgical system will generally take into account the relationship between the state of the focus mechanism and the distance between the endoscope tip and the focal point. Referring now to FIGS. 1 and 15, there may be a variety of (typically non-linear) deterministic compensation and correction curves for the camera/endoscope combination that relate particular focus settings to positions of an object in focus relative to the endoscope. This information can be used to maintain focus during movements of the object or endoscope. For example, for a first non-linear compensation curve, if the endoscope moves two inches radially away from the point of initial focus, moving from a separation distance between the tip of the endoscope and the initial focus point of two inches to a separation distance of four inches, the focusing mechanism will generally move a first amount to compensate for this two inch radial movement. However, if the endoscope moves so as to increase the separation distance by two additional inches, from four inches of separation to six inches of separation between the endoscope tip and the initial focus point, the focus setting may change by a second, different amount on as to compensate for this additional two inch movement. Furthermore, the rate of change in focus setting and the absolute focus setting for a given distance may depend on other variable factors, such as a magnification setting, or the like.

The focus setting/distance relationship graphically illustrated in FIG. 15 may be developed in a variety of different ways. For example, the system may be tested at different magnification settings or the like throughout a range of focus settings to identify the associated distances, or the distances may be incrementally changed with appropriate focus settings being determined, measured, and recorded. In addition to parametric empirical studies, analysis of the optical train of the image capture device using ray tracing or wavefront analytical techniques might also be employed. Still further alternatives may be available, including acquiring at least a portion of the data embodying the relationship of FIG. 15 from the supplier of one or more components of the image capture device.

As can be understood with reference to FIG. 8, purely lateral movement of the endoscope or focus point so as to provide the surgeon or system operator with a view of the surgical site that is from a different angle, or the like, need not necessarily affect the focus setting of the camera, particularly if the endoscope tip remains at a constant distance from the desired focus point at the surgical site. However, if a movement of the endoscope involves both lateral and longitudinal axial movement of the endoscope, only the axial movement may be taken into consideration in adjusting the focus mechanism to maintain the focus at the initial point of focus.

The "stay in focus" functionality described above, which may allow (for example) telesurgical system 1 to maintain focus at a point in space despite movement of the image capture device, may be initiated in response to an input from the surgeon, such as the pressing of a button of input device 4. Activation of the button would inform the processor 5 that the system operator O desires that the point of focus be maintained at the location on which the endoscope and camera are focused at the time the button is actuated. The input device may be embodied in a variety of different structures, including multiple buttons, a reprogrammable button, a cursor or other object on a visual display such as a graphic user interface, a voice control input, or a variety of other input devices. Additionally, the "stay in focus" input device (or some other input structure) could be used to designate one or more of a number of different settings corresponding to different points of focus. Hence, after working at a site performing an anastomosis, for example, the surgeon might desire to pull the endoscope away from the site to provide a wider view of the surgical site, and then to move to some other specific location within the surgical site that was outside the initial field of view. Processor 5 may remember a plurality of positions to be used as focus points for these differing views. The memory of processor 5 may store two or more, three or more, or a large number of positions to be used as alternative focus points.

A variety of modifications of the system illustrated in FIG. 1 may also be provided. For example, in addition or instead of the focus encoder/actuator 8 coupled to image capture device 2, a magnification encoder/actuator may be coupled to a variable magnification structure of the image capture device. The variable magnification structure may comprise a selectable magnification optical train such as those using movable turrets having a plurality of alternative magnification lenses, zoom lens systems, and electronic pixel variation system (sometimes referred to as an electronic zoom), or the like. Along with discrete magnification variation systems, continuous zoom systems may also be implemented. Continuous zoom systems may be more easily implemented in a single-channel endoscope than in a 2-channel or stereoscopic endoscope and camera system, although maintaining relative optical magnification of left and right eyes within a relatively tight correlation across the zoom range may allow the use of continuous zoom stereoscopic systems.

In a preferred embodiment, image capture device 2 has a first magnification setting and second magnification setting which differs from the first setting. An exemplary embodiment includes a dual magnification camera head. Dual magnification camera heads may have an optimum focus depth. At the optimum focus depth, switching from one magnification to another magnification of a dual magnification camera head does not affect the focus depth and does not require refocusing. However, switching magnifications when the camera is focused a point that differs significantly from the optimum focus depth may result in image quality degradation until the focus is adjusted, the image capture device is moved to bring the surgical site back into focus, or the like.

In response to changes in magnification, as sensed by a magnification encoder/actuator and as transmitted in signal form to processor 5, the focus of image capture device 2 may be driven robotically using focus encoder/actuator 8 so as to maintain focus at the desired focus point. The change in focus may occur automatically without input (other than that used to alter magnification) by system operator O, and may compensate for the switch in magnification using a relationship such as that illustrated schematically in FIG. 15. This can be achieved by taking advantage of sensors and/or actuators associated with the focus and/or magnification systems of image capture device 2, per the direction of processor 5. By knowing where the camera is focused for the first magnification setting, the processor 5 can determine the appropriate focusing mechanism state for the second magnification setting so as to maintain the focus at the desired separation distance from the endoscope tip, the desired point in space, or the like. Thus, using information from focus and/or magnification sensors, processor 5 can control the image capture device 2 to refocus or maintain focus of the focusing mechanism so that the desired focus point remains in focus despite any magnification change.

A variety of still further alternative embodiments may also be provided. For example, a telesurgical system similar to system 1 of FIG. 1 may permit focus to be maintained when one endoscope optical train that has been coupled to a camera head is exchanged for another endoscope train having differing optical and focus characteristics than the first. The optical characteristics of the endoscope structure may be programmed into a memory of the endoscope structure and communicated to the processor of the telesurgical system when the endoscope structure is mounted or coupled to the system using techniques similar to those described in U.S. patent application Ser. No. 10/839,727, filed on May 4, 2004, and assigned to the assignee of the subject application under the title "Tool Memory-Based Software Upgrades for Robotic Surgery," the full disclosure of which is incorporated herein by reference.

Some embodiments of the autofocus system may rely on encoders or the like which provide information on the relative position of the camera, focus mechanism, magnification mechanism, or the like. As the system may only maintain focus relative to an initial point of focus, the system processor 5 need not necessarily know (for example) what the absolute state or position of the camera focusing mechanism is during use. In some embodiments, this may be acceptable during at least some modes of operation. In others, absolute position or state information regarding (for example) the magnification system, the focus system, or the like may be addressed by having the mechanism run to a limit or calibrated stop, either manually or automatically (for example on power-up). This may allow the camera head focusing mechanism and/or processor 5 to determine where the endoscope tip and/or focus point are relative to other objects in the surgical field of view. Other embodiments may obtain absolute focusing mechanism state information using a potentiometer or the like. In some embodiments, the focus mechanism may be driven using the absolute state information, for example, so as to instruct the image capture device to focus at a particular location in space.

While described primarily with reference to optical endoscopes having an electronic camera head with a charge couple device (CCD) or the like, a variety of alternative image capture devices may also be employed. For example, the image capture device may make use of a remote imaging modality such as ultrasound, X-ray or fluoroscopy, or the like, with one exemplary remote imaging embodiment employing a Polaroid™ XS 70 ultrasound system.

Information regarding the focus point of image capture device 2 may be used for a variety of purposes. For example, a surgeon or other system operator O will often have the camera focused on the portion of the surgical site at which he or she is working at the time. Knowing the depth at which the surgeon is working (for example, by identifying the separation distance between an endoscope and the focus point) can be used to optimize or tailor other surgical systems to operate at the identified depth or location. For example, U.S. Pat. No. 6,720,988 entitled "A Stereo Imaging System and Method for Use in Telerobotic Systems", the full disclosure of which is incorporated herein by reference, describes a method and apparatus for adjusting the working distance of a stereoscopic endoscope having two light channels. Working distance compensation is typically manually adjusted. By knowing the depth at which the surgeon is working, however, and based on the focal point at which the endoscope is focused, the system processor may drive the working distance compensation system to correspond to the focus distance so as to provide a more coherent stereoscopic image to the system operator.

Other examples of subsystems which may be included in telesurgical system 1 and which may benefit from information regarding the focus distance include repositioning of the robotic arms and joints responsible for movement of the surgical tools (so that the arms are positioned optimally for working at the desired depth), adjusting the motion scale of movement so that the operator's hand movements and input into input device 4 appear in proportion to the surgical site as displayed by display 3, irrigation at the surgical site at an appropriate distance from an integrated irrigation/endoscope structure, insufflation, alteration of tool wrist/elbow positioning (particularly in systems having excess degrees of freedom), and the like. Additional potential uses of focus depth information include optimization or tailoring of illumination (so as to deposit an appropriate amount of light), optimization of the camera sensor (for example, a CCD, a CMOS, or the like), and so on. Many of these structures may be implemented using a tangible media (such as a magnetic disk, an optical disk, or the like) embodying machine readable code with software instructions for performing one, some, or all of the method steps described herein, often in combination with associated electronic, digital, and/or analog signal processing hardware.

In many embodiments, the devices, systems, and methods described herein will be useful for telepresence systems in which an image of a working site is displayed to a system operator at a position relative to master input controls manipulated by the operator in such a manner that the operator substantially appears to be directly manipulating the robotically controlled end effectors. Such telepresence systems are described, for example, in U.S. Pat. No. 5,808,665, the full disclosure of which is incorporated herein by reference, as well as in U.S. Pat. No. 6,424,885, which has previously been incorporated herein by reference. In these telepresence systems, surgeons and other system operators may benefit from having their hand movements appear to directly correspond to the movements of the end effectors at the working site. A telepresence system may, for example, permit a surgeon to select various scales of relative movement between the master input controls and the slave manipulator end effector movements. For example, an input for selection between motion scales of 1:1, 2:1, and 5:1 may be provided for a particular telepresence system, so that for every centimeter of movement of an end effector of the slave there are 1, 2, and 5 centimeters of movement by the master input devices, respectively. Proper selection of motion scales may facilitate the performance of (for example) very delicate surgical operations on small vasculature using the robotic tools, and may also help keep the surgical tool movements with an appearance of being substantially connected to movement of the master input devices.

While a plurality of alternatively selectable motion scales may serve many telepresence systems quite will, still further refinements are possible. For example, the motion scale of movement between the end effector and input device may benefit from changes when the camera head magnification changes, when the endoscope zooms for a closer view of the surgical site, or when the endoscope is simply brought closer to a tool or tissue of interest. If the movement scaling is not changed in these circumstances, the instruments may not appear as connected to the surgeon's hand movements as might be ideal. Fortunately, this can be overcome by automatically adjusting the scale of movement appropriately with changes in the state of the image capture device, such as a magnification or optical scale of the endoscope and/or camera head, a location of the endoscope tip relative to a worksite or tool, or the like. This may help maintain the appearance that movements of the surgeon's hands are more directly associated with movements of the tools or treatment probes at the surgical site. Such association can be provided when the system takes advantage of the depth of focus based on the information provided from focus encoder/actuator 8 of image capture device 2, and relating that depth information to a corresponding master/slave proportional movement scaling. In some embodiments, the depth information may be related to a predetermined set of correspondence information (such as optical scale factors) between the master and slave movements. The system may be pre-programmed with either a mathematical relationship between different motion scales for a given depth of field based on the geometric parameters of the system, or with a data lookup table. Regardless, the system may adjust the scale of movement for the desired relationship between focus depth and movement scaling, with this function optionally being referred to as autoscaling.

Autoscaling may be modified by having the endoscope remain focused on the surgical instruments even when those instruments move. For example, the autofocus mechanism may focus on targets located on the instruments, as was previously described regarding the establishment of an initial point of focus. The autofocus function can also continually track motion of the end effectors during the surgical procedure. Without movement of the endoscope, the focus mechanism may be adjusted according to the movement of the end effectors (for example) of a tissue manipulation instrument or probe 6, and thus according to the corresponding movements of the targets on those probes. With such an arrangement, information from the focus encoder/actuator 8 may be able to provide continuous information to processor 5 regarding where the surgical tool or probe is located. This information may then be used to autoscale movements of the surgical tools at the surgical site.

Keeping track of a position of the surgical tool relative to a tip of the endoscope using a focus encoder/actuator 8 (or other focus system vehicles) may also be employed in the end effector controller described herein. For example, the focusing mechanism state data may provide information regarding a Z axis dimension of the controller. X and Y position information of the tool within a field of view of the endoscope can be captured using image processing pattern recognition techniques. Alternative surgical tool location techniques may be described in U.S. Pat. No. 5,402,801, the full disclosure of which is also incorporated herein by reference. In some embodiments, rather than tracking the position of the surgical tool end effectors relative to the endoscope tip by assuming all of the positions of the robotic linkages relative to a common point on the base, the relative separation and/or positioning of the endoscope and tool (see FIG. 8) may at least in part be determined from the imaging system, for example, through pattern recognition and by determining the focal depth of the image capture device as focused on the surgical tool. Predicting tool position in the final displayed endoscope view analytically using robotic data (such as by summing the mechanical vectors of the linkages according to the joint state data) may in at least some cases by unacceptably imprecise in practice due to the combination of optical and mechanical tolerances and error buildup. Optical recognition methods and system may reduce or even be immune to these tolerance or accuracy issues.

As noted above, many telesurgical systems may employ a plurality of surgical tools. Since the tool tips or end effectors are not always positioned in the same plane perpendicular to longitudinal axis of the endoscope, one tool may be designated as the focal tool. The focal tool may bear a master target on which the camera will automatically focus, and a camera may focus on that tool unless instructed otherwise by processor 5 and/or system operator O. The other tool(s) may carry secondary targets, and if desired, may be designated by the operator as the master tool on which the endoscope is to focus. While some telerobotic systems may, for example, touch a tip of a probe or a tool to the tip of the endoscope to establish the relative positions of these structures, use of the data from image capture device 2 by, for example, focusing on the tool tip either manually or automatically, followed by using position information from the image capture device and its associated manipulator may provide information regarding where the tool tip is located relative to the endoscope. The processor 5 may make use of this information to autoscale or adjust the movement scaling between the input device and the end effector or tip of the tool.

The ability of processor 5 to determine absolute depths of focus may also enhance the ability of the surgeon to control the endoscope movement. For example, endoscopes may be controlled by instructing the endoscope system to move verbally, followed by a verbal instruction to the endoscope system to halt the movement. Similar instructions may be given, for example, by actuating a joy stick or depressing a foot pedal for the desired duration of movement and then releasing the joy stick or halting the pressure on the foot pedal. Alternative input systems may instruct an endoscope to move an incremental distance for each verbal or other input instruction. The AESOP™ endoscope system commercially sold by Computer Motion of Goleta, Calif., and subsequently serviced by Intuitive Surgical of Sunnyvale, Calif., is an example of a voice-controlled endoscope system. These systems may, for example, benefit from techniques described herein so as to allow the system operator to (for example) verbally instruct the system to "focus one inch," "focus three inches," or the like. Such instructions may provide an absolute focus instruction, and similar absolute focus instructions may be input through other devices such as a keypad, input buttons, dial settings, or the like.

Still further alternative embodiments may be provided. For example, stand alone voice activation may be provided so as to control magnification. A number of discrete positions may be available, or continuous zoom may be provided, allowing the system operator to instruct the endoscope system to zoom in, zoom out, focus in, focus out, or the like, often through the use of a system in which the zoom and/or focus is robotically driven as generally described above. In general, a plurality of specific positions (position 1, position 2, or the like) or magnifications (wide, medium, narrow, or the like) may be provided with voice activation optionally providing absolute (rather than relative) image capture device input. Along with altering the depth of focus in response to changes in magnification, information regarding the depth of focus may be used by the surgeon for a variety of uses in medical applications. The desired relative motion scaling between the input device and end effector movements (or autoscale) may be determined based on the focal depth for a variety of relationships. The relationship may be linear, quadratic, or the like, and may be determined empirically, analytically, or from information provided by suppliers.

Figure 16:
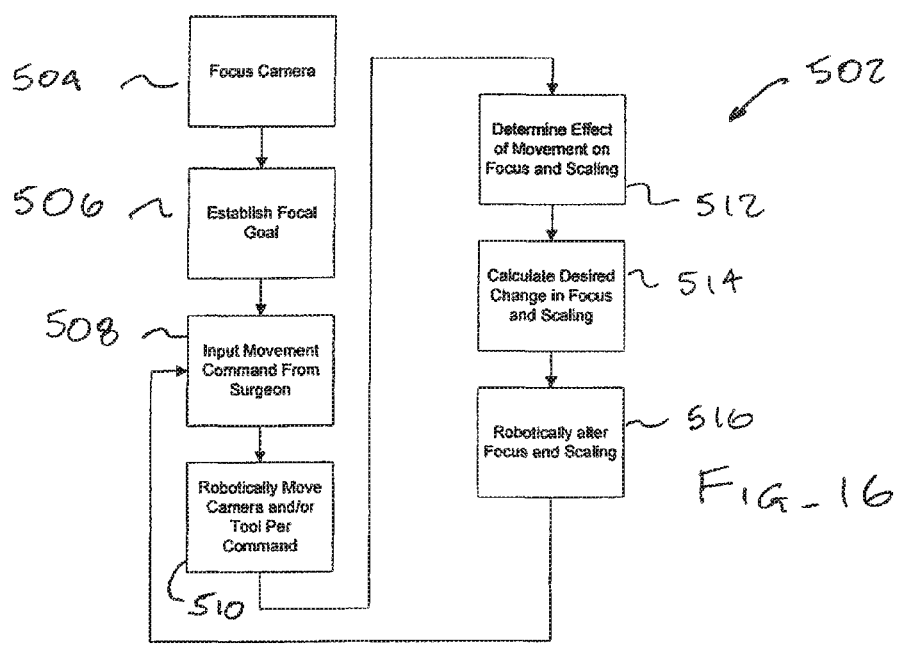
FIG. 16 is a flowchart schematically illustrating a method for adjusting a focus and/or a movement scaling of the telesurgical system of FIG. 1.

Referring now to FIG. 16, an exemplary method for adjusting focus and/or motion scaling of a telerobotic or telesurgical system 502 begins with focusing of the camera at an initial focus depth, as described above. The camera may be focused manually by the system operator or using any of the wide variety of commercially available autofocus techniques. A focal goal is established 506, such as maintaining the initial focus point at a fixed point in space, maintaining the focus at a moving robotic tool structure, maintaining focus on a tissue, or the like. Such focals will often be embodied in a processor of the telerobotic system using software and/or hardware, and may be selected from a plurality of focal goals by the system operator.

In response to an input movement command from the system operator 508, the system processor calculates an appropriate movement of the image capture device and/or another robotic end effector 510. The effect of the robotic movement on focus and motion scaling is calculated 512, for example, by determining a post-movement separation distance between the endoscope tip and the desired focus point.

Using the established focal goal 506 and the determined effect of movement on motion focus or scaling 512, the processor can calculate a desired change in focus and motion scaling. For example, where the goal is to maintain the focus at a fixed location in space, and the processor has determined that the endoscope has moved so as to result in the current focal state being focused at one inch short of the desired focus point, the processor can use the relationship between the focus state and the desired focal distance graphically represented in FIG. 15 so as to calculate a change in the focal state. In other embodiments, when the change in the position of the robotic arm results in the focus point being half the distance to the endoscope camera as was present prior to the move, with a linear relationship between separation distance producing a tool image as presented to the system operator which is twice as large after the endoscope movement, the system processor (for example) change a motion scaling ratio between movement at an input device and movement of the tool from 2:1 to 1:1. A variety of alternative changes in desired focusing and/or motion scaling 514 may similarly be calculated.

Once the desired change in focus and/or motion scaling has been calculated, the system processor sends signals to the focus or optical scaling mechanism of the image capture device 516 so as to effect the change. Changes to the focus or optical scaling of the image capture device may be effected by any of a wide variety of actuators, and confirmation of the change may be transmitted to the processor using an encoder, potentiometer, or any of a wide variety of sensor or signal transmitting structures.

While exemplary embodiments have been described in some detail for clarity of understanding and by way of example, a variety of modifications, changes, and adaptations will be obvious to those of skill in the art. Hence, the scope of the present invention is limited solely by the appended claims.

What is claimed is:

1. A robotic system comprising:
   an image capture device;
   an actuator configured to adjust a magnification setting of the image capture device;
   a robotic linkage movably supporting the image capture device;
   at least one sensor for generating a sensor signal indicating movement of the robotic linkage;
   a processor configured to determine, based on the sensor signal, a change in distance between the image capture device and an initial focus point of the image capture device, the processor further configured to adjust the magnification setting of the image capture device by controlling said actuator according to a predetermined relationship between the magnification setting of the image capture device and the change in distance;
   the predetermined relationship being derived from parametric empirical measurements of the image capture device.

2. The system of claim 1, further comprising a master input device, the robotic linkage configured to move said image capture device at least in part in response to movement of the master input device.

3. The system of claim 1, the processor further configured to adjust the magnification setting in response to an input from an operator of the system.

4. The system of claim 2, the input comprising a button press on the master input device.

5. The system of claim 1, further comprising a plurality of image capture devices each having an adjustable magnification setting, each image capture device removably coupleable to the linkage, the at least one sensor further comprising sensors for detecting movement of each image capture device, wherein the processor is further configured to adjust the magnification setting of each image capture device in response to signals sent from the at least one sensor to the processor.

6. The system of claim 1, wherein the image capture device has a first magnification setting and a second magnification setting, and wherein the processor is further configured to adjust a focus setting of the image capture device in response to a change in the magnification setting so as to maintain a focus point of the image capture device.

7. The system of claim 1, further comprising a display coupled to the image capture device, wherein a display scale of an object shown on the display varies with a separation distance between a focal point of the image capture device and the image capture device.

8. The system of claim 7, further comprising:
   an input device for inputting a master/slave movement command;
   the processor further configured to determine a movement of the robotic linkage corresponding to the movement command per a motion scale factor, the processor further configured to alter the motion scale factor in response to relative movement between the initial focus point and the image capture device so as to compensate for changes in the display scale.

9. The system of claim 1, further comprising:
an input device coupled to the processor for inputting a movement command;
a robotic manipulator coupled to the processor, the processor further configured to determine a movement of the robotic manipulator corresponding to the movement command according to a motion scale factor, the processor further configured to alter the motion scale factor in response to the movement of the image capture device so as to compensate for changes in the display scale.

10. The system of claim 1, the image capture device comprising a selectable magnification optical train having a plurality of alternative magnification lenses.

11. The system of claim 1, the image capture device comprising a selectable magnification optical train having an electronic pixel variation system.

12. The system of claim 1, the image capture device comprising a continuous zoom system for adjusting the magnification setting.

13. The system of claim 1, the image capture device further having an adjustable focus setting, the processor configured to adjust the focus setting in response to a change in the magnification setting.

14. The system of claim 1, the image capture device further having an adjustable focus setting, the processor further configured to adjust the focus setting according to a predetermined relationship between the focus setting and a change in the magnification setting.

15. The system of claim 1, the at least one sensor comprising an encoder of the robotic linkage.

16. The system of claim 1, the at least one sensor comprising a potentiometer of the robotic linkage.

17. The system of claim 1, the actuator configured to mechanically adjust the magnification to a given magnification setting.

* * * * *